(12) United States Patent
Peterson et al.

(10) Patent No.: US 11,952,630 B2
(45) Date of Patent: Apr. 9, 2024

(54) DRIED COMPOSITIONS CONTAINING FLAP ENDONUCLEASE

(71) Applicant: Gen-Probe Incorporated, San Diego, CA (US)

(72) Inventors: Patrick Peterson, San Marcos, CA (US); Tony Luu, San Diego, CA (US); Matthias Jost, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 142 days.

(21) Appl. No.: 17/746,400

(22) Filed: May 17, 2022

(65) Prior Publication Data

US 2022/0275448 A1 Sep. 1, 2022

Related U.S. Application Data

(63) Continuation of application No. 17/674,521, filed on Feb. 17, 2022, now abandoned, which is a continuation of application No. 16/613,744, filed as application No. PCT/US2018/033549 on May 18, 2018, now Pat. No. 11,286,526.

(60) Provisional application No. 62/540,478, filed on Aug. 2, 2017, provisional application No. 62/508,990, filed on May 19, 2017, provisional application No. 62/508,975, filed on May 19, 2017.

(51) Int. Cl.
*C12Q 1/68* (2018.01)
*C12Q 1/6844* (2018.01)
*C12Q 1/6876* (2018.01)

(52) U.S. Cl.
CPC ......... *C12Q 1/6876* (2013.01); *C12Q 1/6844* (2013.01); *C12Q 2527/125* (2013.01); *C12Y 207/07007* (2013.01)

(58) Field of Classification Search
None
See application file for complete search history.

(56) References Cited

U.S. PATENT DOCUMENTS

| | | | |
|---|---|---|---|
| 5,102,788 A | 4/1992 | Cole | |
| 5,556,771 A | 9/1996 | Shen et al. | |
| 5,593,824 A | 1/1997 | Treml et al. | |
| 5,861,251 A | 1/1999 | Park et al. | |
| 5,876,992 A | 3/1999 | De Rosier et al. | |
| 6,153,412 A | 11/2000 | Park et al. | |
| RE37,872 E | 10/2002 | Franks et al. | |
| 6,684,524 B1 | 2/2004 | Sennhenn et al. | |
| 6,908,759 B2 | 6/2005 | Jang | |
| 6,910,720 B2 | 6/2005 | Shimei et al. | |
| 7,964,350 B1 | 6/2011 | Fekete et al. | |
| 8,187,557 B2 | 5/2012 | Van Alta et al. | |
| 8,426,134 B2 | 4/2013 | Piepenburg et al. | |
| 8,470,261 B2 | 6/2013 | Eshoo et al. | |
| 8,900,525 B2 | 12/2014 | Ponaka et al. | |
| 9,279,145 B2 * | 3/2016 | Eshoo | C12Q 1/6806 |
| 11,286,526 B2 | 3/2022 | Peterson et al. | |
| 2005/0069898 A1 | 3/2005 | Moon et al. | |
| 2005/0106596 A1* | 5/2005 | Skrzypczynski | C12Q 1/6827 435/6.1 |
| 2006/0068398 A1 | 3/2006 | McMillan | |
| 2006/0147955 A1* | 7/2006 | Allawi | C12Q 1/6823 435/91.2 |
| 2007/0259348 A1 | 11/2007 | Phadke et al. | |
| 2011/0136118 A1 | 6/2011 | Kreader et al. | |
| 2014/0011184 A1 | 1/2014 | DeCastro | |
| 2014/0087382 A1* | 3/2014 | Allawi | C12Q 1/6851 435/6.12 |
| 2014/0113294 A1* | 4/2014 | Horton | C12P 19/34 435/6.12 |
| 2014/0186821 A1* | 7/2014 | Daum | C12Q 1/6806 435/6.12 |
| 2014/0295419 A1 | 10/2014 | Zhang et al. | |
| 2015/0315636 A1* | 11/2015 | Nadeau | C12Q 1/6858 435/6.11 |
| 2015/0361511 A1* | 12/2015 | Lee | C12Q 1/701 435/6.12 |
| 2015/0368693 A1* | 12/2015 | Johnson | C12Q 1/6848 435/6.12 |
| 2016/0032269 A1 | 2/2016 | Gong | |
| 2017/0121704 A1* | 5/2017 | Allawi | C12Q 1/6837 |
| 2017/0204384 A1* | 7/2017 | Skirgaila | C12N 9/1252 |
| 2017/0349936 A1* | 12/2017 | Daum | C12N 15/1003 |
| 2021/0155910 A1* | 5/2021 | Pyle | C12P 19/34 |

FOREIGN PATENT DOCUMENTS

| | | |
|---|---|---|
| EP | 1374827 A2 | 1/2004 |
| JP | 2008-504046 | 2/2008 |
| JP | 2011-526492 | 10/2011 |

(Continued)

OTHER PUBLICATIONS

Chinese Office Action dated Sep. 12, 2023 from corresponding Chinese Application No. 201880024871.3 (11 pages).
Examination Report dated Jul. 21, 2021 from corresponding German Application No. 1120180025977 (2 pages).
Office Action dated Jan. 13, 2021 from corresponding Japanese Application No. 2019-557762 (2 pages).
Preliminary Rejection dated Mar. 30, 20213 from corresponding Korean Application No. 10-2019-7031802 (3 pages).
Office Action dated Oct. 16, 2020 from corresponding Canadian Application No. 3059977 (5pages).
Office Action dated Oct. 12, 2021 from corresponding Canadian Application No. 3059977 (5 pages).
PCT/US2018/033549 International Search Report and Written Opinion dated Jul. 20, 2018.
Klatser, et al., "Stabilized, Freeze-Dried PCR Mix for Detection of Mycobacteria," Journal of Clinical Microbiology, vol. 36, No. 6, p. 1798-1800, (Jun. 1998).

(Continued)

*Primary Examiner* — Aaron A Priest
(74) *Attorney, Agent, or Firm* — Jeffrey E. Landes; Alston & Bird LLP

(57) ABSTRACT

There is disclosed a composition of an aqueous solution comprising, consisting or consisting essentially of a flap endonuclease, a bulking agent and an organic buffer, wherein the aqueous solution has an inorganic salt concentration of 5 mM or less and wherein the composition is substantially free of glycerol.

21 Claims, No Drawings

(56) References Cited

FOREIGN PATENT DOCUMENTS

| | | | | |
|---|---|---|---|---|
| JP | 2012-529887 | | 11/2012 | |
| JP | 2015-533507 | | 11/2015 | |
| WO | WO 2006/003439 A2 | | 1/2006 | |
| WO | WO 2006/119280 A2 | | 11/2006 | |
| WO | WO2007/005626 | | 1/2007 | |
| WO | WO 2008/090340 A2 | | 7/2008 | |
| WO | WO 2008/155524 A1 | | 12/2008 | |
| WO | 2009117327 A2 | | 9/2009 | |
| WO | WO2009/117327 | | 9/2009 | |
| WO | WO2010/106788 | | 9/2010 | |
| WO | WO2010/141940 | | 12/2010 | |
| WO | WO2010/144682 | | 12/2010 | |
| WO | WO2013/105588 | | 7/2013 | |
| WO | WO2014/114956 | | 7/2014 | |
| WO | WO-2014114956 A1 | * | 7/2014 | ............. A61K 47/26 |
| WO | WO2016/034892 | | 3/2016 | |
| WO | WO2017/136782 | | 8/2017 | |

OTHER PUBLICATIONS

Richard, et al., Thermal stability landscape for Klenow DNA polymerase as a function of pH and salt concentration, Biochimica et Biophysica Acta, 1764, p. 1546-1552, (2006).

BD Sprint Advantage PCR Products User Manuel, BD Biosciences Clontech, pp. 1-22, (2003).

BD Sprint Advantage 96 Plate, Versatile PCR enzyme mix in a high-throughput format, BD Biosciences Clontech, (2002).

GE Healthcare, "Illustra puReTaq Ready-To-Go PCR Beads," Product Booklet, pp. 1-22, (2006).

PCT/US2017/016592 International Search Report and Written Opinion dated Apr. 3, 2017.

GB1701910.0 Combined Search and Examination Report dated Dec. 5, 2017.

U.S. Appl. No. 16/613,744 Notice of Allowance dated Nov. 18, 2021.

U.S. Appl. No. 16/613,744 Corrected Notice of Allowance dated Nov. 24, 2021.

* cited by examiner

DRIED COMPOSITIONS CONTAINING FLAP ENDONUCLEASE

CROSS-REFERENCE TO RELATED PATENT APPLICATIONS

The present application is a continuation of U.S. application Ser. No. 17/674,521, filed Feb. 17, 2022, which is a continuation of U.S. application Ser. No. 16/613,744, filed Nov. 14, 2019, which is a 371 National Stage entry of International Application No. PCT/US2018/033549 with an international filing date of May 18, 2018, which claims the benefit of each of provisionals 62/508,975, filed May 19, 2017, 62/508,990, filed May 19, 2017, 62/540,478 filed Aug. 2, 2017, each hereby incorporated by reference in their entireties for all purposes.

BACKGROUND

Commercial kits for performing nucleic acid based assays often contain reagents such as enzymes, nucleotides, detergents, buffers, primers, probes and inorganic salt, including $MnCl_2$, $MgCl_2$, NaCl, and KCl (Innis et al, (1990) PCR Protocols: A Guide to Methods and Applications, Ch. 1, Optimizations of PCRs).

Nucleic-acid-based assays can be "nucleic acid amplification-based assays," i.e., assays that utilize one or more steps for amplifying a nucleic acid target sequence. Various amplification methods for use in nucleic acid based assays are known in the art. Alternatively, a nucleic-acid-based assay can be a "non-nucleic acid amplification-based assay," i.e., an assay that does not rely on any step for amplifying a nucleic acid target sequence. An exemplary non-nucleic acid amplification-based assay is a "cleavage-based assay," which is an assay that relies on specific cleavage, by a flap endonuclease, of a linear duplex cleavage structure formed by the specific hybridization of overlapping oligonucleotides to a target nucleic acid. In these assays, an invader oligonucleotide (also referred to as an "invader probe") is designed to stably anneal to a target nucleic acid at assay reaction temperature. Signal probe oligonucleotides containing a target hybridizing sequence and a non-target-hybridizing flap region that overlays the invader oligonucleotide, are designed with a melt temperature that is approximately that of the assay temperature. As a consequence, the signal probes are in a state of annealing/dissociating from the target nucleic acid at reaction conditions. When a signal probe is annealed to the target nucleic acid in the presence of a flap endonuclease, the non-target hybridizing flap region is cleaved in an overlap-dependent manner by the flap endonuclease to release a cleavage product. The cleaved flap region then anneals with a hairpin configured probe comprising a signalling moiety and a quenching moiety (often referred to as a "FRET probe") to form an overlap between a portion of the cleaved flap portion and the portion of the FRET probe that is joined to one of the signalling moiety or the quenching moiety. In the presence of a flap endonuclease, the FRET probe is cleaved in an overlap-dependent manner to release one of the signalling moiety or quenching moiety from the FRET probe, thereby resulting in a detectable signal. Because an excess of signal probe and FRET probe relative to the invader probe is used in these assays, they are often referred to as signal amplification assays. The principles of cleavage-based assays are well-known in the art, and exemplary assays are described in, for example, Lyamichev et al. (Nat. Biotechnol. 17:292-296, 1999), Ryan et al. (Mol. Diagn. 4: 135-144, 1999), Allawi et al. (J. Clin. Microbiol. 44:3443-3447, 2006), U.S. Pat. No. 5,846,717 & 6,706,471 to Brow et al., and U.S. Pat. No. 5,614,402 to Dahlberg et al. Cleavage-based assays include, e.g., the commercially available Invader® assays (Hologic, Inc., Marlborough, MA).

In some circumstances, it can be desirable to carry out "amplification-based assays" (e.g. PCR) and "non-amplification-based assays" (e.g. assays using Cleavase® enzyme) in the same reaction. Cleavase® enzyme is a thermostable structure-specific endonuclease that cleaves at the junctions between single- and double-stranded deoxyribonucleic.

Magnesium ions have been reported to increase activity of polymerases and other enzymes. Potassium chloride has been reported to facilitate nucleic acid hybridizations. A number of inorganic salts have been reported to protect proteins under various conditions of stress including heat, chaotropic agent exposure and lyophilization (Liu et al (2007) FEBS Letters. 581:1047; Kanaya et al (1996) J. Biol. Chem. 271:32729; Innis et al, (1990) PCR Protocols: A Guide to Methods and Applications, Ch. 1, Optimizations of PCRs; Menendez et al (1998) J. Biol. Chem. 273:167; Janeway et al (1993) Biochemistry. 32:1601, Fox et al (1971) J. Biol. Chem. 246:5739, Chang et al (2002) J. Biol. Chem. 277:277:4663, Rutter et al (1958) J. Biol. Chem. 233:374, Huszar et al (1981) J. Virol. 37:580-588, Wang (2000) Int. J. Pharmaceutics. 203:1-60). Salts are also used in "amplification-based assays" and "non-amplification-based assays" assays. By way of example, typical reaction conditions to carry out the Invader® assay include potassium chloride in the enzyme stock and magnesium chloride in the reaction buffer.

However, the stability of a lyophilized substance is affected by the hygroscopicity of any salts present in the lyopholized cake. Hygroscopicity of a lyophilized substance in turn affects the time available to package the lyophilized substance, and affects the duration and conditions under which the lyophilized substance can be stored and shipped. The undesired rehydration of a lyophilized substance negatively impacts the activity of lyophilized components. To minimize the negative impact from undesired rehydration of a lyophilized substance, long term storage of such substances is usually performed with refrigeration.

The present invention seeks to provide improvements in lyophilized compositions, especially when used in nucleic acid based assays—such as non-amplification-based assays or non-amplification-based assays combined with amplification based assays.

SUMMARY

There is disclosed a composition of an aqueous solution comprising, consisting or consisting essentially of a flap endonuclease, a bulking agent and an organic buffer, wherein the aqueous solution has an inorganic salt concentration of 6 mM or less and wherein the composition is substantially free of glycerol.

Suitably, the aqueous solution further comprises at least one oligonucleotide useful for performing a molecular assay.

Suitably, the aqueous solution further comprises at least one oligonucleotide useful for performing a nucleic acid based assay.

Suitably, the flap endonuclease is a Cleavase® enzyme.

Suitably, the composition further comprises at least one polymerase.

Suitably, the at least one polymerase includes a polymerase present in the aqueous solution at a concentration from about 0.10 U/ul to about 0.25 U/ul in the aqueous solution.

Suitably, the at least one polymerase includes a polymerase present in the aqueous solution at a concentration selected from: 0.11 U/ul, 0.12 U/ul, 0.14 U/ul, 0.146 U/ul, 0.1687 U/ul, 0.2 U/ul, and 0.022 U/ul.

Suitably, the at least one polymerase includes a polymerase that is a hot-start polymerase.

Suitably, the hot-start polymerase is a recombinant Taq DNA polymerase bound by an antibody that specifically blocks polymerase activity of the polymerase.

Suitably, the hot-start polymerase is a chemically modified recombinant Taq DNA polymerase, wherein the chemical modification inhibits polymerase activity of the polymerase.

Suitably, the at least one polymerase includes a reverse transcriptase present in the aqueous solution, suitably, at a concentration from about 0.1 U/ul to about 4.0 U/ul.

Suitably, the reverse transcriptase is an AMV reverse transcriptase.

Suitably, the reverse transcriptase is an MMLV reverse transcriptase.

Suitably, the at least one oligonucleotide includes an invader probe.

Suitably, the sequence of the invader probe is partially or completely complementary to a target nucleic acid sequence.

Suitably, the at least one oligonucleotide includes a signalling probe.

Suitably, the sequence of the signalling probe is partially complementary to a target nucleic acid sequence.

Suitably, the sequence of the signalling probe comprises a flap region.

Suitably, the flap region at least partially overlaps with an invader probe.

Suitably, the at least one oligonucleotide includes a FRET probe.

Suitably, the sequence of the FRET probe is partially complementary to the flap region of a signalling probe.

Suitably, the FRET probe comprises a label covalently joined thereto.

Suitably, the label is a fluorescent molecule.

Suitably, the label is located at the 5' end of the FRET probe.

Suitably, the FRET probe comprises a quencher molecule covalently joined thereto, within quenching proximity to the fluorescent molecule, and capable of quenching at least partially fluorescence from the fluorescent molecule.

Suitably, the at least one oligonucleotide includes a target capture probe.

Suitably, the target capture probe has a target hybridizing portion that specifically or non-specifically hybridizes to a target nucleic acid under stringent conditions.

Suitably, the target capture probe has a target hybridizing portion that non-specifically hybridizes to a target nucleic acid under stringent conditions.

Suitably, the non-specific target hybridizing portion of the target capture probe comprises randomly arranged K nucleotides or randomly arranged R nucleotides (IUPAB-IUB ambiguity codes).

Suitably, the aqueous solution comprises two or more oligonucleotides for performing a multiplex molecular assay.

Suitably, the bulking agent is trehalose.

Suitably, the bulking agent is present at a concentration from about 0.2 M to about 0.5 M, suitably about 0.36 M.

Suitably, the aqueous solution comprises an inorganic salt concentration of 6 mM or less. Suitably, the aqueous solution comprises an inorganic salt concentration between about 6 mM to about 0.5 mM.

Suitably, the inorganic salts are present at a mass per microliter of from about 0.373 µg/µl about 0.029 µg/µl.

Suitably, the inorganic salt is sodium chloride, suitably, wherein the sodium chloride is present at a mass per microliter of from about 0.35 ug/ul to about 0.029 ug/ul, suitably about 0.32 ug/ul.

Suitably, the inorganic salt is potassium chloride, suitably, wherein the potassium chloride is present at a mass per microliter of from about 0.373 ug/ul of potassium chloride to about 0.019 ug/ul of potassium chloride, suitably about 0.03 ug/ul.

Suitably, the aqueous solution contains from about 0.135 ug/ul of sodium ions to about 0.006 µg/µl of sodium ions, suitably, about 0.127 ug/ul.

Suitably, the aqueous solution contains from about 0.196 ug/ul of potassium ions to about 0.010 ug/ul of potassium ions, suitably about 0.016 ug/ul.

Suitably, the aqueous solution contains from about 0.355 ug/ul chloride ions to about 0.009 ug/ul chloride ions, suitably about 0.337 ug/ul.

Suitably, the aqueous solution comprises an inorganic salt concentration of 4 mM or less.

Suitably, the aqueous solution comprises a mass per microliter of inorganic salt from about 0.298 µg/µl to about 0.234 µg/µl.

Suitably, the aqueous solution comprises a mass per microliter of chloride ions from about 0.284 µg/µl to about 0.071 µg/µl.

Suitably, the aqueous solution comprises an inorganic salt concentration of 3 mM or less.

Suitably, the aqueous solution comprises a mass per microliter of inorganic salt from about 0.224 µg/µl to about 0.175 µg/µl.

Suitably, the aqueous solution comprises a mass per microliter of chloride ions from about 0.213 µg/µl to about 0.053 µg/µl.

Suitably, the aqueous solution comprises an inorganic salt concentration of 2 mM or less.

Suitably, the aqueous solution comprises a mass per microliter of inorganic salt from about 0.149 µg/µl to about 0.117 µg/µl.

Suitably, the aqueous solution comprises a mass per microliter of chloride ions from about 0.142 µg/µl to about 0.036 µg/µl.

Suitably, the aqueous solution comprises an inorganic salt concentration of 1 mM or less.

Suitably, the aqueous solution comprises a mass per microliter of inorganic salt from about 0.075 µg/µl to about 0.058 µg/µl.

Suitably, the aqueous solution comprises a mass per microliter of chloride ions from about 0.071 µg/µl to about 0.018 µg/µl.

Suitably, the aqueous solution comprises an inorganic salt concentration of 500 µM or less.

Suitably, the aqueous solution comprises a mass per microliter of inorganic salt from about 0.037 µg/µl to about 0.029 µg/µl.

Suitably, the aqueous solution comprises a mass per microliter of chloride ions from about 0.036 µg/µl to about 0.009 µg/µl.

Suitably, the inorganic salt concentration of the aqueous solution is less than 1 mM sodium chloride.

Suitably, the aqueous solution does not contain sodium chloride.

Suitably, the aqueous solution contains less than 1 mM magnesium ions.

Suitably, the aqueous solution contains less than 0.1 mM magnesium ions.

Suitably, the aqueous solution further comprises deoxynucleotide triphosphates (dNTPs).

Suitably, the dNTPs include dATP at a concentration of from 0.1 mM to 0.5 mM in the aqueous solution, suitably about 0.28 mM to about 0.46 mM.

Suitably, the dATP is at a concentration of 0.3 mM to 0.4 mM in the aqueous solution, e.g, 0.375 mM.

Suitably, the dNTPs include dGTP at a concentration of from 0.1 mM to 0.4 mM in the aqueous solution.

Suitably, the dGTP is at a concentration of 0.3 mM to 0.4 mM in the aqueous solution, suitably 0.29 to 0.46 mM, e.g, 0.375 mM.

Suitably, the dNTPs include dCTP at a concentration of from 0.1 mM to 0.4 mM in the aqueous solution, suitably 0.29 to 0.46 mM.

Suitably, the dCTP is at a concentration of 0.3 mM to 0.4 mM in the aqueous solution, e.g., 0.375 mM.

Suitably, the dNTPs include dTTP at a concentration of from 0.1 mM to 0.4 mM in the aqueous solution, suitably 0.2 to 0.37 mM, e.g, 0.284 mM.

Suitably, the dNTPs include dUTP at a concentration of from 0.1 mM to 0.4 mM in the aqueous solution, suitably 0.125 to 0.234 mM, e.g., 0.182 mM.

Suitably, the flap endonuclease is present in the aqueous solution at about 0.010 µg/µl to about 0.050 ug/ul, suitably at about 0.12 ug/ul to 0.047 ug/ul.

Suitably, the flap endonuclease is present in the aqueous solution at about 0.030 µg/µl to about 0.04 µg/µl, suitably, wherein the flap endonuclease is present in the aqueous solution at about 0.030 µg/µl to about 0.035 µg/µl.

Suitably, the organic buffer is 3-(N-morpholino)propanesulfonic acid (MOPS) buffer.

Suitably, the MOPS buffer is present at a concentration of from 10 to 20 mM in the aqueous solution, suitably at a concentration of 12.5 mM to 20 mM in the aqueous solution.

Suitably, the organic buffer is tris(hydroxymethyl)aminomethane (Tris) buffer.

Suitably, the Tris buffer is present at a concentration of from 40 mM to 60 mM in the aqueous solution, suitably at a concentration of 50 mM in the aqueous solution.

Suitably, the composition contains a globular protein.

Suitably, the globular protein is bovine serum albumin (BSA).

Suitably, the bovine serum albumin (BSA) is non-acetylated BSA, suitably, ultrapure non-acetylated BSA.

Suitably, globular protein is present in an amount of 0.40 to 0.60 µg/µl, suitably, 0.50 µg/µl.

Suitably, the composition comprises, consists or consists essentially of a Cleavase® enzyme, trehalose, MOPS buffer, dNTPs, an inorganic salt concentration of 5 mM or less and wherein the composition is substantially free of glycerol.

Suitably, the composition comprises, consists or consists essentially of a Cleavase® enzyme present in the aqueous solution at about 0.030 µg/µl, trehalose present in a concentration of about 0.3M, MOPS buffer in a concentration of about 12.5 mM, dNTPs at a concentration of about 0.3 mM each, optionally, dATP, dGTP, and dCTP are at about 0.375 mM, dTTP is about 0.284 mM and dUTP is about 0.182 mM, an inorganic salt concentration of 5 mM or less and wherein the composition is substantially free of glycerol.

Suitably, the composition comprises, consists or consists essentially of a Cleavase® enzyme, trehalose, Tris buffer, dNTPs, bovine serum albumin, an inorganic salt concentration of 5 mM or less and wherein the composition is substantially free of glycerol.

Suitably, the composition comprises, consists or consists essentially of a Cleavase® enzyme present in the aqueous solution at about 0.030 µg/µl, trehalose present in a concentration of about 0.3M, Tris buffer in a concentration of about 50 mM, dNTPs at a concentration of about 0.3 mM each, optionally, dATP, dGTP, and dCTP are at about 0.375 mM, dTTP is about 0.284 mM and dUTP is about 0.182 mM, bovine serum albumin at about 0.5 µg/µl, an inorganic salt concentration of 5 mM or less and wherein the composition is substantially free of glycerol.

Suitably, the composition comprises, consists or consists essentially of Cleavase®, trehalose, MOPS buffer, dNTPs, bovine serum albumin, an inorganic salt concentration of 5 mM or less and wherein the composition is substantially free of glycerol.

Suitably, the composition comprises, consists or consists essentially of Cleavase® present in the aqueous solution at about 0.035 µg/µl, trehalose present in a concentration of about 0.36M, MOPS buffer at a concentration of about 15 mM, dNTPs at a concentration of about 0.38 mM each, bovine serum albumin at about 0.5 µg/µl, an inorganic salt concentration of 5 mM or less and wherein the composition is substantially free of glycerol.

Suitably, the composition includes alpha-cyclodextrine, for example at a concentration of 0.1-0.5 ug/ml.

There is also disclosed a dried form of the composition according to the present disclosure. By way of example, 24 ul of an aqueous solution described herein is dried to provide a dried composition having a mass in the range of from about 0.003 g to about 0.004 g, from about 0.0032 g to about 0.0037 g, 0.0033 g, 0.0034 g, 0.0035 g, or 0.0036 g. It is understood that a plurality of dried compositions made from aliquots of a single bulk aqueous solution will have variations in the mass of each dried composition. By way of example, two or more 24 ul aliquots of a bulk aqueous solution will each be dried to separately provide a dried composition having a mass in the range of from about 0.003 g to about 0.004 g. Thus, the average weight of each of the plurality of dried pellets is in the range of from about 0.003 g to about 0.004 g, from about 0.0032 g to about 0.0037 g, 0.0033 g, 0.0034 g, 0.0035 g, or 0.0036 g. Changing the concentration of a component in the aqueous solution will result in a change to the mass of the dried composition. For example, changing the concentration of an enzyme to optimize the enzyme activity for use in a particular reaction may result in a change to the mass of the dried composition. Similarly, changes in the type of component used can result in changes in the mass of the dried composition. For example using different flap endonucleases can require concentration changes to provide a desired enzyme activity level. Changing the concentration and/or type of one or more of the various components is understood to fall within the instant disclosure, and thus resultant changes to the mass of the dried composition is similarly understood to fall within the instant disclosure.

There is also disclosed a dried composition comprising, consisting or consisting essentially of a flap endonuclease, a bulking agent and an organic buffer, wherein the one or more inorganic salts are present in the dried composition at a mass that is 0.350% or less of the total mass of the dried composition and wherein the dried composition is substantially free of glycerol.

Dried compositions are useful for nucleic acid based assays following reconstitution. Dried compositions surprisingly provide robust results following prolonged exposure to humid environments. The dried form of the compositions are useful in nucleic acid based assays following exposure to a humid environment, wherein the absolute humidity level of the humid environment is greater than 2.3 grams of water per cubic meter of air for a period of time of up to 3 hours; preferably for a period of time from 90 minutes to 180 minutes; preferably about 90 minutes; of preferably about 180 minutes. Dried compositions surprisingly provide robust results following prolonged incubation times of the pre-dried aqueous solution.

Suitably, one or more inorganic salts are present in the dried composition at a mass that is in from about 0.311% to about 0.024% of the total mass of the dried composition.

Suitably, the one or more inorganic salts are selected from the group consisting of: sodium chloride, potassium chloride and both sodium chloride and potassium chloride.

Suitably, the dried composition further comprises at least one oligonucleotide useful for performing a molecular assay.

Suitably, the dried composition further comprises at least one oligonucleotide useful for performing a nucleic acid based assay.

Suitably, the at least one oligonucleotide includes a probe oligonucleotide, suitably at least two probe oligonucleotides.

Suitably, the probe oligonucleotide(s) is partially or completely complementary to a target nucleic acid sequence.

Suitably, the flap endonuclease is a Cleavase® enzyme.

Suitably, the dried composition further comprises at least two probe oligonucleotides capable of annealing to a target nucleic acid to form a three-dimensional structure that can be recognized by the flap endonuclease.

Suitably, the dried composition further comprises at least one polymerase.

Suitably, the at least one polymerase includes a polymerase present in the aqueous solution at a concentration from about 0.10 U/µl to about 0.2 U/µl in the aqueous solution.

Suitably, the at least one polymerase includes a polymerase present in the aqueous solution at a concentration selected from about 0.1 U/ul to about 0.25 U/ul.

Suitably, the at least one polymerase includes a polymerase that is a hot-start polymerase.

Suitably, the hot-start polymerase is a recombinant Taq DNA polymerase bound by an antibody that specifically blocks polymerase activity of the polymerase.

Suitably, the hot-start polymerase is a chemically modified recombinant Taq DNA polymerase, wherein the chemical modification inhibits polymerase activity of the polymerase.

Suitably, the at least one polymerase includes a reverse transcriptase present in the aqueous solution, suitably, at a concentration from about 0.1 U/µl to about 0.6 U/µl.

Suitably, the reverse transcriptase is an AMV reverse transcriptase.

Suitably, the reverse transcriptase is an MMLV reverse transcriptase.

Suitably, the at least one oligonucleotide includes a detection probe.

Suitably, the at least one oligonucleotide includes a detection probe.

Suitably, the sequence of the detection probe is partially or completely complementary to a target nucleic acid sequence.

Suitably, the detection probe comprises a label covalently joined thereto.

Suitably, the label is a fluorescent or chemiluminescent molecule.

Suitably, the label is located at the 5' end of the detection probe and an internal quencher molecule.

Suitably, the at least one oligonucleotide includes an invader probe.

Suitably, the sequence of the invader probe is partially or completely complementary to a target nucleic acid sequence.

Suitably, the at least one oligonucleotide includes a signalling probe.

Suitably, the sequence of the signalling probe is partially complementary to a target nucleic acid sequence.

Suitably, the sequence of the signalling probe comprises a flap region.

Suitably, the flap region at least partially overlaps with an invader probe.

Suitably, the at least one oligonucleotide includes an FRET probe.

Suitably, the sequence of the FRET probe is partially complementary to the flap region of a signalling probe.

Suitably, the FRET probe comprises a label covalently joined thereto.

Suitably, the label is a fluorescent molecule.

Suitably, the label is located at the 5' end of the FRET-probe. Suitably, the FRET probe comprises a quencher molecule covalently joined thereto, within quenching proximity to the fluorescent molecule, and capable of quenching at least partially fluorescence from the fluorescent molecule Suitably, the at least one oligonucleotide includes a target capture probe.

Suitably, the target capture probe has a target hybridizing portion that specifically or non-specifically hybridizes to a target nucleic acid under stringent conditions.

Suitably, the target capture probe has a target hybridizing portion that non-specifically hybridizes to a target nucleic acid under stringent conditions.

Suitably, the non-specific target hybridizing portion of the target capture probe comprises randomly arranged K nucleotides or randomly arranged R nucleotides.

Suitably, the composition comprises oligonucleotides for performing a multiplex molecular assay.

Suitably, the bulking agent is trehalose.

Suitably, the dried composition further comprises deoxynucleotide triphosphates (dNTPs).

Suitably, the organic buffer is 3-(N-morpholino)propanesulfonic acid (MOPS) buffer.

Suitably, the organic buffer is tris(hydroxymethyl)aminomethane (Tris) buffer.

Suitably, the dried composition contains a globular protein.

Suitably, the globular protein is bovine serum albumin (BSA).

Suitably, the bovine serum albumin (BSA) is non-acetylated BSA, suitably, ultrapure non-acetylated BSA.

There is also disclosed a method of forming a mixture for use in performing a nucleic acid based assay, the method comprising combining a reconstitution solution and the dried composition described herein, wherein the reconstitution solution comprises at least one inorganic salt.

Suitably, the reconstitution solution comprises an inorganic salt concentration of less than 1 mM.

Suitably, the reconstitution solution comprises magnesium ions.

Suitably, the reconstitution solution comprises $MgCl_2$ at a concentration from about 5 mM to about 15 mM, suitably, from 9 mM to 10 mM or 9-12 mM, optionally 11.25 mM.

Suitably, the reconstitution solution is selected from the group consisting of: methyl paraben at a concentration from about 0.012% w/v to about 0.020% w/v, propyl paraben at a concentration from about 0.006% w/v to about 0.010% w/v, absolute ethanol at a concentration from about 0.20% v/v to about 0.30% v/v, or a combination thereof.

Suitably, the concentration of the methyl paraben in the reconstitution solution is 0.016% w/v.

Suitably, the concentration of the propyl paraben in the reconstitution solution is 0.008% w/v.

Suitably, the concentration of the absolute ethanol is present in the reconstitution solution at about 0.26% v/v.

There is also disclosed a method for preparing a dried composition for use in performing a nucleic acid based assay, the method comprising the steps of: (i) freezing an aqueous solution of the present disclosure, thereby forming a frozen form of the aqueous solution; and (ii) exposing the frozen form from step (i) to lyophilization conditions, thereby forming a dried composition.

Suitably, the dried composition is exposed to a humid environment, wherein the absolute humidity level of the humid environment is greater than 2.3 grams of water per cubic meter of air at 30 degrees C.

Suitably, the dried composition is exposed to the humid environment for up to 3 hours.

Suitably, the method comprises the step of storing the dried composition in a sealed vessel.

There is also disclosed a method for preparing a dried composition for use in performing a nucleic acid based assay, comprising the step of: drying the aqueous solution described herein using a drying method selected from the group consisting of: dehydration, desiccation, lyophilization, and spray-drying, thereby forming a dried composition.

Suitably, the drying method is lyophilization and the dried composition is a lyophilized composition.

Suitably, the method further comprises the step of storing the dried composition in a sealed vessel.

There is also disclosed a kit for use in performing a nucleic acid based assay, the kit comprising a first vessel containing the dried composition as described herein, and a second vessel containing a reconstitution solution comprising $MgCl_2$ at a concentration from about 3.8 mM to about 14.4 mM, suitably, about 9.4 mM or about 11.25.

Suitably, the first vessel is a multiwell plate comprising one or more wells.

Suitably, each of the one or more wells contains a dried single unit dose pellet that contains a percent mass of inorganic salt to mass of pellet of 0.311% or less.

Suitably, the first and second vessels are incorporated within a device adapted for automated transfer of the reconstitution solution from the second vessel into the first vessel.

Suitably, each of the one or more wells contains a dried single unit dose pellet with a weight of from about 0.000125 g to about 0.000667 g for each microliter of aqueous solution that was dried to form the dried single unit dose pellet in each well.

Suitably, each of the one or more wells contains a dried single unit dose pellet each having a weight in the range of from about 0.003 g to about 0.004 g, from about 0.0032 g to about 0.0037 g, 0.0033 g, 0.0034 g, 0.0035 g, or 0.0036 g.

There is also disclosed a dialysis composition comprising, consisting or consisting essentially of an aqueous solution containing an organic buffer, a bulking agent, chloride ions and a chelating agent.

Suitably, the bulking agent is trehalose.

Suitably, the bulking agent is present at a concentration from about 100 mM to 300 mM, suitably, 200 mM.

Suitably, the organic buffer is tris(hydroxymethyl)aminomethane (Tris) buffer.

Suitably, the Tris buffer is present at a concentration of from 10 mM to 30 mM in the aqueous solution, suitably at a concentration of 20 mM in the aqueous solution. Suitably, the pH is about 8.0.

Suitably, the chloride ions are KCl.

Suitably, the KCl is present at a concentration of about 40 to 60 mM, suitably, 50 mM.

Suitably, the chelating agent is EDTA.

Suitably, the EDTA is present in the aqueous solution at a concentration from 0.05 to 0.2 mM, suitably, 0.1 mM.

Suitably, the composition comprises a flap endonuclease, suitably, a Cleavase® enzyme.

There is also disclosed a method for preparing a substantially glycerol-free flap endonuclease composition comprising: (i) providing an aqueous solution comprising, consisting or consisting essentially of a flap endonuclease and glycerol; (ii) dialysing the aqueous solution into the dialysis composition as described herein; and (iii) obtaining a substantially glycerol-free flap endonuclease composition.

Suitably, the aqueous solution in step (i) contains from about 0.0 to about 0.5% (w/v) glycerol, suitably, about 0.35% (w/v) glycerol, more suitably less than 0.2% (w/v) glycerol.

There is also disclosed the use of the dried composition described herein for preparing a dried flap endonuclease-containing composition.

There is also disclosed the use of the dried composition described herein combined with a reconstitution solution for performing a nucleic acid based assay.

There is also disclosed the use of the dialysis composition described herein for preparing a substantially glycerol-free flap endonuclease composition.

Definitions

The term "about" indicates insubstantial variation in a quantity of a component of a composition not having any significant effect on the activity or stability of the composition.

A "bulking agent" provides a matrix for the deposit of proteins and other reagents during drying and storage. (Carpenter et al (2002) Rational design of stable lyophilized protein formulations. Kluwer Academic/Plenum, New York, pp. 109-133). Bulking agents can be used to form a product "cake" or other structure, and can prevent protein from being lost from the vial during drying and increase protein stability.

A "chelating agent" is an agent that sequesters divalent ions, such as $Mg^{2+}$ or $Mn^{2+}$ required for enzyme activity.

The terms "lyophilization," "lyophilized," and "freeze-dried" refer to a process by which the material to be dried is first frozen and then the ice or frozen solvent is removed by sublimation in a vacuum environment. "Lyophilisate" refers to a lyophilized substance.

The term "stringent" in reference to nucleic acid hybridization (including "stringent hybridization conditions" or "stringent conditions") refers to conditions where a specific oligonucleotide is able to hybridize with target nucleic acids over other nucleic acids present in the test sample. It will be appreciated that these conditions may vary depending upon factors including the GC content and length of the oligonucleotide, the hybridization temperature, the composition of the hybridization reagent or solution, and the degree of hybridization specificity sought. Appropriate hybridization conditions are well known in the art for probes, oligonucleotides, target capture oligonucleotides, blockers and other oligonucleotides, may be predicted based on sequence composition, or can be determined by using routine testing methods (e.g., Sambrook et al., *Molecular Cloning, A Laboratory Manual*, 2nd ed. (Cold Spring Harbor Laboratory Press, Cold Spring Harbor, NY, 1989) at §§ 1.90-1.91, 7.37-7.57, 9.47-9.51 and 11.47-11.57, particularly §§ 9.50-9.51, 11.12-11.13, 11.45-11.47 and 11.55-11.57).

The term "cleavage structure" refers to a structure that is formed by the interaction of a number of nucleic acids to form a configuration wherein two of the nucleic acids each contain a nucleobase configured to hybridize at a single nucleobase position on a third nucleic acid such that an overlap is formed between the first two nucleic acids where the resulting non-hybridized flap region (e.g., cleavage structure) is cleavable by a flap endonuclease. The cleavage structure is a substrate for specific cleavage by the flap endonuclease, in contrast to a nucleic acid molecule that is a substrate for non-specific cleavage by agents such as phosphodiesterases, which cleave nucleic acid molecules without regard to secondary structure (i.e., no formation of a duplex structure is required). For a discussion of a cleavage structure, as well as other aspects of a flap endonuclease detection assay, please see U.S. Pat. No. 5,846,717.

A "flap endonuclease," as used herein, refers to a class of nucleolytic enzymes that act as structure-specific 5' endonucleases on nucleic acid structures with a duplex containing a single-stranded 5' overhang, or flap, on one of the strands that is displaced by another strand of nucleic acid (i.e., such that there are overlapping nucleotides where the adjacent first and second probes hybridize to a target). A flap endonuclease may also be referred to as a "5' endonuclease" or by the acronym "FEN" for short. FENs catalyze hydrolytic cleavage of the phosphodiester bond at the junction of single- and double-stranded nucleic acid, releasing the overhang, or flap. FENs are reviewed by Ceska and Savers (Trends Biochem. Sci. 23:331-336, 1998) and Liu et al. (Annu. Rev. Biochem. 73:589-615, 2004).

An "overlap region" or "flap region" consists of the base or bases of the first probe oligonucleotide (e.g., a signal probe) that hybridize to the target and are overlapped by the second probe oligonucleotide (e.g., an invader probe). The base on the 3' end of the second probe oligonucleotide determines the end of the overlap region and may or may not hybridize to the target.

A "first probe oligonucleotide," in reference to a cleavage-based assay, refers to an oligonucleotide that interacts with a target nucleic acid to form a cleavage structure (e.g. a signal probe) in the presence of a "second probe oligonucleotide" that hybridizes to a region upstream of the first probe oligonucleotide (e.g. an invader probe). When annealed to the target nucleic acid, the first probe oligonucleotide and target form a cleavage structure and cleavage by a flap endonuclease can occur within the first probe oligonucleotide. In the presence of an overlapping second probe oligonucleotide upstream of the first probe oligonucleotide along the target nucleic acid, the site of cleavage within the first probe oligonucleotide will occur after the last overlapping base (cleavage depends on at least one overlapping base of the second probe with target-hybridized bases of the first probe). In addition to a target-hybridizing region that hybridizes to a target sequence within the target nucleic acid, a first probe oligonucleotide contains a non-target-hybridizing region at the 5' end (also referred to as a "flap region"). When first and second probe oligonucleotides are annealed to a target nucleic acid, site-specific cleavage by a flap endonuclease occurs to generate a cleavage product that contains the flap region and the overlap region of the first probe oligonucleotide.

A "second probe oligonucleotide" in reference to a cleavage-based assay, refers to an oligonucleotide that contains a sequence at its 3' end that, when annealed to the target nucleic acid, overlaps the 5' end of the target-hybridizing sequence within a downstream first probe oligonucleotide; typically, these regions will compete for hybridization to the same segment along a complementary target nucleic acid. The second probe can, in some instances, be used as a primer as well as an invader probe. The 3' terminal nucleotide of the second probe oligonucleotide may or may not base pair with a nucleotide in the target nucleic acid. In some variations, only the 3' terminal nucleotide overlaps the 5' end of the target-hybridizing sequence of the first probe oligonucleotide. The cleaved second probe oligonucleotide can be involved in a secondary reaction where they act as probes on a fluorescent resonance energy transfer cassette (e.g. a FRET probe or FRET cassette) leading to the formation of an overlapping structure that is recognised by a Cleavase® enzyme. When the FRET cassette is cleaved a fluorophore is released from a quencher on the FRET cassette generating a fluorescence signal.

As used herein, the term "FRET cassette" refers to a hairpin oligonucleotide that contains a fluorophore moiety and a nearby quencher moiety that quenches the fluorophore. Hybridization of a cleavage product with a FRET cassette produces a secondary substrate for the flap endonuclease. Once this substrate is formed, the 5' fluorophore-containing base is cleaved from the cassette, thereby generating a fluorescence signal.

An "amplification oligomer" is a primer or promoter primer that can support template-dependent replication. An amplification oligomer pair is a pair of such oligomers that support template dependent replication of opposing strands of a template. Multiplex amplification is amplification performed with multiple amplification oligomer pairs simultaneously.

A "detection probe" is an oligonucleotide that can hybridize to an amplification product or an initial target nucleic acid to reveal presence or amount of the amplification product. Such detection probes often incorporate a molecule giving a fluorescent or other detectable signal in which case they are referred to as detectably labelled probes.

A "primer-probe set" is a combination of primers and detection probe configured for generating an amplification product from a template nucleic acid.

"Reconstitution time" is the time that is required to rehydrate a dried formulation with a solution to result in a solution that is free of particles or turbidity to the naked eye.

"Relative Fluorescence Units (RFU)" are a measure of unquenched fluorophore. In nucleic acid based amplification reactions, the presence of a product is determined by measuring RFU at a number of cycle times (Ct).

"Ct" refers is the number of cycles that was required to reach the exponential phase in a real time PCR. Ct is inversely related to the amount of analyte in a sample.

"Positivity", when in reference to assay reaction results, refers to the percent of samples that crossed over into the exponential threshold, in a test involving a plurality of samples. For example, when the plurality of samples is twelve samples, and when the number of samples crossing over was determined to be six, positivity is "50%."

A "single unit dose" or "SUD" refers to a volume of a reaction mixture that is used to perform an assay on a single sample. A single unit dose can be in liquid form or in dried form. By way of example, a single unit dose can be a dried pellet containing reagents useful for the detection of a single sample in a single vessel.

"LOD" is limit of detection of an analyte. LOD+1 is the LOD that the user has detected plus one log. In other words, LOD+1 is ten times the number of analytes that is the LOD.

Compositions disclosed as including dTTP and dUTP can include dTTP or dUTP or both at the concentrations indicated. Likewise when a composition is disclosed as containing dTTP or dUTP, the disclosure should be understood as alternatively including a composition including both dTTP and dUTP at the indicated concentrations.

DETAILED DESCRIPTION

I. General

The present disclosure is based, at least in part, on the finding that instability of prior lyophilized kits for performing nucleic acid based assay is due to the presence of inorganic salts. These salts can result in undesired hybridization products or other by-products before, during and after drying. These salts also make a dried composition hygroscopic such that it absorbs water, thus requiring limited exposure to humidity, refrigerated or deep freeze storage and/or storage in the presence of a desiccant. The presence of water and salts causes the enzyme component of such kits to lose activity prematurely and can also facilitate hybridization of nucleic acids in such kits to each other. The present disclosure has overcome these problems by drying reagents for conducting a nucleic acid based assay from bulk reagents essentially free of inorganic salts. Such salts are supplied on reconstitution of the dried composition. Contrary to the expectation that inorganic salts are necessary for stability of enzymes used for nucleic acid based assays, it has been found that reaction mixtures dried essentially free of inorganic salt can be stored long term above freezing, with full or substantial retention of activity on reconstitution.

II. Bulk Reagents & Dried Pellets.

Bulk reagents (sometimes referred to as prelyophilized mixtures, solutions, aqueous solutions or compositions) according to the disclosure typically include a flap endonuclease, a bulking agent, an organic buffer. Bulk reagents may or may not also include one or more nucleic acids and/or dNTPs. Bulk reagents may include chelators and RNase inhibitors.

Such bulk reagents are essentially free of inorganic salts meaning the concentration of inorganic salt individually and collectively is less than 5 mM and preferably less than 1 mM. Preferably, the concentration of Mg2+ is less than 1 mM, less than 0.5 mM, less than 0.1 mM or less than 0.05 mM. Preferably, the concentration of Na+ is less than 1 mM, less than 0.5 mM, less than 0.1 mM or less than 0.05 mM. Preferably, the concentration of K+ is less than 1 mM, less than 0.5 mM, less than 0.1 mM or less than 0.05 mM. Preferably, the concentration of Cl— is less than 1 mM, less than 0.5 mM, less than 0.1 mM or less than 0.05 mM.

Such bulk reagents are substantially free of glycerol. As used herein, the term "substantially free" means that glycerol is not present in an amount generally used in an enzyme preparation. Suitably, the glycerol is present in amount of less than 5% (w/v), less than 4% (w/v), less than 3% (w/v), less than 2% (w/v), less than 1% (w/v), less than 0.5% (w/v), less than 0.1% (w/v) or less than 0.01% (w/v). Suitably, the glycerol is present in amounts that are not detectable using conventional methods that are known in the art. For example, the Abcam (Cambridge, UK) Glycerol Assay Kit can be used to measure free glycerol concentration by enzymatically oxidizing glycerol to generate a product which reacts with a probe to generate color and fluorescence. The kit can detect 50 pmol-10 nmol of glycerol in various samples. Suitably, the glycerol is present in a concentration of less than 50 pmol.

Nucleotides for incorporation into a reaction mixture are typically provided as dNTPs. Exemplary concentrations for dNTPs are 0.1 to 0.4 mM of dATP, suitably, 0.3 to 0.4 mM dATP, suitably, 0.29 to 0.46 mM dATP; 0.1 to 0.4 mM of dGTP, suitably, 0.3 to 0.4 mM dGTP, suitably, 0.29 to 0.4 mM dGTP; 0.1 to 0.4 mM of dCTP, suitably, 0.3 to 0.4 mM dCTP, suitably, 0.29 to 0.4 mM dCTP; 0.1 to 0.4 mM of dTTP, suitably, 0.2 to 0.3 mM dATP; and 0.1 to 0.4 mM of dUTP, suitably, suitably, 0.125 to 0.234 mM dUTP. Exemplary concentrations in a 1.5× lyophilization mix or final reaction (i.e., after reconstitution in 1.5× volume) are as follows.

|  | In lyo mix (mM) | In reaction (mM) |
| --- | --- | --- |
| dATP | .375 | .25 |
| dGTP | .375 | .25 |
| dCTP | .375 | .25 |
| dTTP | .284 | .189 |
| dUTP | .182 | .122 |

Such mixtures can be customized for any type of reaction that uses a flap endonuclease. Such mixtures can be customized for any type of reaction that uses a flap endonuclease and a polymerase.

Flap endonucleases are commercially available or can be prepared by a user. A flap endonuclease is not restricted to enzymes having solely 5' nuclease activity. For example, the flap endonuclease may be a native DNA polymerase having 5' nuclease activity e.g., Taq DNA polymerase, E. coli DNA polymerase I) or a modified DNA polymerase having 5' nuclease activity by lacking synthetic activity (e.g., a Cleavase® enzyme).

Such mixtures can be customized for different types of amplification including PCR, RT-PCR and transcription mediated amplification by the choice of polymerase enzyme and other components.

DNA polymerase enzymes are commercially available or can be prepared by a user. One example of a polymerase enzyme is a Taq polymerase commercially available from Qiagen (Germantown, MD, cat #201203). Another example of a Taq polymerase is commercially available as GoTaq® G2 Flexi DNA polymerase (Promega, Madison, WI, cat #M7801). Other DNA polymerases that are commercially available include, but are not limited to, Tth DNA polymerase (e.g., Sigma-Aldrich, St. Louis, MO, cat #11480022001), and chimeric DNA polymerases such as Phusion® High-Fidelity DNA Polymerase (NEB, Ipswich, MA, cat #M0530S). Also commercially available are hot-start DNA polymerase enzymes. For example, a Taq polymerase is commercially available as GoTaq® Hot Start Polymerase (Promega, cat #M5001). The GoTaq® Hot Start polymerase is an antibody mediated hot start enzyme, where the Taq polymerase is bound to an antibody that blocks polymerase activity. The blocking antibody is denatured using high heat, thus during the initial heat step of a PCR reaction, the antibody is denatured and polymerase activity is restored. Various antibodies can be used with hot start method, for example, TAQSTART antibody (Clontech Laboratories, Mountain View, CA, cat #R028A). Similarly, other hot start polymerase enzymes are available, including chemically-mediated hot start polymerases. Equivalent polymerase and antibodies are available from a variety of commercial sources and, alternatively, can be prepared by the user.

Reverse transcriptase enzymes are commercially available or can be prepared by a user. Examples of commercially available reverse transcriptase include, but are not limited to, MMLV (Maloney Murine Leukemia Virus) reverse transcriptase & SuperScript® III Reverse Transcriptase (e.g., ThermoFisher Scientific, Carlsbad, CA, cat #s 28025-013 & 18080-044), MMLV RT (Sigma-Aldrich, cat #M1302), AMV Reverse Transcriptase (NEB, Ipswich, MA, cat #M0277S), and GoScript™ reverse transcriptase (Promega, cat #A50003). GoScript reverse transcriptase includes a reverse transcriptase and a set of reagents for synthesis of first-strand cDNA optimized for quantitative PCR amplification. Equivalent reverse transcriptase and reagents are available from various commercial sources and, alternatively, can be prepared by the user.

Exemplary concentrations for a flap endonuclease in single unit doses are between about 0.01 μg/μl to about 1.0 μg/μl, suitably, between about 0.01 μg/μl and about 0.8 μg/μl, or between about 0.01 μg/μl and about 0.6 μg/μl, or between about 0.01 μg/μl and about 0.4 μg/μl, or between about 0.01 μg/μl and about 0.2 μg/μl, or between about 0.01 μg/μl and about 0.1 μg/μl. More suitably, the concentrations for a flap endonuclease in single unit doses are between about 0.02 μg/μl and about 0.04 μg/μl. More suitably, the concentrations for a flap endonuclease in single unit doses are between about 0.030 μg/μl to about 0.04 μg/μl, more suitably, between about 0.030 μg/μl to about 0.035 μg/μl. Suitably, the flap endonuclease is present in the aqueous solution at about 0.010 μg/μl to about 0.050 ug/ul, suitably at about 0.012 ug/ul to 0.047 ug/ul.

Exemplary concentrations for DNA polymerase enzyme in single unit doses are 0.1-0.2 U/μl (inclusive of all whole and partial numbers therein). For example 0.14 U/μl, 0.146 U/μl and 0.1687 U/μl.

One unit of DNA polymerase is defined as the amount of enzyme required to catalyze the incorporation of 10 nanomoles of dNTPs into acid-insoluble material in 30 minutes at 74 degrees C. Exemplary concentrations of reverse transcriptase enzyme in single unit doses are 0.01 U/μl-1.0 U/μl (inclusive of all whole and partial numbers therein). One unit of reverse transcriptase is defined as the amount of enzyme required to catalyze the transfer of 1 nmol of deoxynucleotide into acid-precipitable material in 10 minutes at 37 degrees C.

A preferred organic buffer is MOPS or Tris.

Suitably, the MOPS buffer is present at a concentration of from about 10 mM to about 20 mM in the aqueous solution, suitably at a concentration of about 12.5 mM to about 15 mM in the aqueous solution.

Suitably, the Tris buffer is present at a concentration of from about 5 mM to about 60 mM in the aqueous solution, suitably at a concentration of from about 40 to 60 mM in the aqueous solution, suitably at a concentration of about 50 mM in the aqueous solution, suitably at a concentration of about 10 mM in the aqueous solution.

Alternative organic buffers that can be incorporated into bulk reagents include phosphate, citrate, acetate, CHES, histidine, and Good's buffers, such as HEPES, MES, tricine, and glycinamide, as well as buffer combinations. Other organic buffers include succinate, citrate, gluconate, phosphate, and the like. Preferred buffers are effective in a pH range from about 6.0 to about 10.0 or about 7.0 to about 9.0; suitably a pH of about 7.5 or 8.0 or 8.5 is used.

A preferred bulking agent is trehalose. Other bulking agents that are contemplated include raffinose, sucrose, mannitol, trehalose plus mannitol, sucrose plus mannitol, sucrose plus glycine, and hydroxyethyl starch. See, Cleland et al (2001) J. Pharm. Sci. 90:310; Meyer et al (2009) Eur. J. Pharm. Sci. 38:29; Webb et al (2003) J. Pharm. Sci. 92:715; Garzon Rodrigues et al (2004) J. Pharm. Sci. 93:684; Qiu et al (2012) Int. J. Pharmaceuticals. 437:51); Van Dijk-Wolthuis et al (1997) Polymer. 38:6235 6242. Hydroxyethyl starch is classified as, hetastarch, hexastarch, pentastarch, and tetrastarch (see, e.g., WO2014/099198 of Chow). The bulking agent is preferably present at a concentration of from about 0.2 M to about 0.5 M, suitably, about 0.2 M to about 0.4 M, suitably about 0.3 M to about 0.4 M, suitably, about 0.47 M, suitably about 0.36 M.

Bulk reagents may include one more nucleic acids—such as probe oligomers, amplification oligomers, capture probes, positive control template, and negative control template and the like. Bulk reagents may include one more nucleic acids for performing a non-amplification based assay including one or more probe oligonucleotides. Bulk reagents may include one more nucleic acids for performing a non-amplification based assay and an amplification based assay including one or more probe oligonucleotides and/or one or more amplification oligomers and/or one or more amplification oligomer pairs and/or multiple amplification oligomer pairs.

Optional additional components of a bulk reagents include RNase inhibitor, detergents, zwitterionic detergents, anionic detergents, cationic detergents, non-ionic detergents, surfactants, primers, probes, template, polymers, biopolymers, oligosaccharides, polysaccharides, poly-glucose, amylose, chelating agent, methyl paraben, and propyl paraben. An exemplary concentration for methyl paraben is 0.01-0.024% by weight, for example about 0.016%, or alternatively, about 0.010%, about 0.014%, about 0.016%, about 0.020%, about 0.024%, and any ranges bordered by these values. An exemplary concentration range of propyl paraben is 0.002-0.016% or 0.008%, or alternatively, about 0.002%, about 0.004%, about 0.006%, about 0.008%, about 0.010%, about 0.012%, about 0.014%, about 0.016% or any range bordered by these values. One unit is defined as the amount of RNasin® Ribonuclease Inhibitor required to inhibit the activity of 5 ng of ribonuclease A by 50%. Activity is measured by the inhibition of hydrolysis of cytidine 2', 3'-cyclic monophosphate by ribonuclease A.

Chelating agents include one or more of EDTA (ethylenediaminetetraacetic acid), EGTA (ethylene glycol tetraacetic acid), EDDS (ethylenediamine-N,N'-disuccinic acid), MGDA (methylglycindiacetic acid), and DTPA (diethylene triamine pentaacetic acid). Exemplary concentrations for chelating agents are from 1.0 mM-2.5 mM. In one embodiment, the use of EDTA is preferred. Suitably, the EDTA is present at a concentration from about 0.05 to about 0.2 mM, suitably, about 0.1 mM.

RNase inhibitor proteins are native and recombinant are 50 kDa proteins that inhibit RNase A family and human placental RNases by noncovalently binding to RNases in a 1:1 ratio (Promega Corp., Madison, WI). See, Botella-Estrada et al (2001) Cancer Gene Ther. 8:278; Polakowski et al (1992) EXS. 61:428. Exemplary concentrations of RNase inhibitor are from about 0.04 U/µl to about 0.4 U/µl.

Bulk reagents can contain detergent at low concentration. Detergents include ionic (cationic or anionic), non-ionic and zwitterionic detergents available from a number of commercial vendors (e.g., Geno Technology, Inc., St. Louis, MO). Examples include, but are not limited to, lithium lauryl sulfate, amprolium hydrochloride, benzalkonium chloride, choline p-toluenesulfonate salt, dodecyltrimethylammonium chloride, 3-[(3-Cholamidopropyl)dimethylammonio]-1-propanesulfonate, ethylhexadecyldimethylammonium bromide, hexadecylpyridinium chloride, hexadecyltrimethylammonium chloride, sodium dodecyl sulfate, hexadecyltrimethylammonium p-toluenesulfonate, Luviquat™, methylbenzethonium chloride, myristyltrimethylammonium bromide, N,N',N'-Polyoxyethylene (10)-N-tallow-1,3-diaminopropane liquid, oxyphenonium bromide, tetraheptylammonium bromide, tetrakis(decyl)ammonium bromide, tricaprylylmethylammonium chloride, Amidosulfobetaine-16, tridodecylmethylammonium chloride, trimethyloctadecylammonium bromideNonidet P-40®, Tween-20®, Tween-80®, Brij-35®, Triton X-100®.

Exemplary volumes of a bulk reagents include about 1 ul, about 5 ul, about 10 ul, about 20 ul, about 24 ul, about 50 ul, about 100 ul, about 200 ul, about 300 ul, about 400 ul, about 500 ul, about 600 ul, about 700 ul, about 800 ul, about 900 ul, about 1,000 ul (1 mL), about 2 mL, about 5 mL, about 10 mL, about 20 mL, about 50 mL, and so on. Reconstituted compositions can be formed at the same volume, a lower volume, or greater volume than the bulk reagents. A lower volume can be about 90%, about 80%, about 60%, about 40%, about 20%, about 10%, or about 5%, relative to the bulk reagents. A greater volume can be about 120%, 140%, 160%, 180%, 200% (2-fold), about 4-fold, about 6-fold, about 8-fold, about 10-fold, about 20-fold, that of the bulk reagents.

A sample to be analyzed can be added to the bulk reagents either before reconstitution, at the same time as reconstitution, or after reconstitution. In a preferred embodiment, the entire dried composition after reconstitution is used for combining with sample, and here the relative volumes of reconstitution solution/sample can be, for example, about 9.9/0.1, 9.8/0.2, 9.5/0.5, 9/1, 8/2, 7/3, 6/4, 5/5, and so on.

Unless otherwise specified, concentrations of reagents in bulk reagents can be for example, 0.0% (an omitted reagent), 0.001%, 0.004%, 0.008%, 0.0012%, 0.0016%, 0.0020%, 0.0030%, 0.0040%, 0.0050%, 0.0060%, 0.0080%, 0.01%, 0.02%, 0.04%, 0.06%, 0.1%, 0.2%, 0.3%, 0.4%, 0.5%, 0.6%, 0.8%, 1%, 2%, 3%, 4%, 5%, and the like. Also provided are reagents that are at "about" the above concentrations, less than the above concentrations, more than the above concentrations, ranges involving any two of the above concentrations.

An exemplary bulk reagent composition is substantially free of glycerol, has an inorganic salt concentration of 5 mM or less and has 0.1-0.4 mM and suitably about 0.3 mM of each of dATP, dGTP dCTP and dUTP or dTTP and 0.02 µg/µl-0.40 ug/µL flap endonuclease, suitably about 0.03 µg/µl flap endonuclease. Some compositions include a bulking agent, suitably trehalose, at about 0.2 M to about 0.4 M, suitably about 0.3 M. Some compositions include a buffer, suitably MOPS buffer, suitably at a pH of about 7.5.

Another exemplary bulk reagent composition is substantially free of glycerol, has an inorganic salt concentration of 5 mM or less and has 0.1-0.4 mM and suitably about 0.375 mM of each of dATP, dGTP dCTP and about 0.182 mM dUTP or about 0.284 mM of dTTP, 0.02 µg/µl-0.40 ug/µL flap endonuclease, suitably about 0.035 µg/µl flap endonuclease, and 0.1 U/µl to 0.2 U/µl, suitably, 0.146 U/µl polymerase. Some compositions include a bulking agent, suitably trehalose, at about 0.2 M to about 0.4 M, suitably about 0.3 M. Some compositions include a buffer, suitably MOPS buffer, suitably at a pH of about 7.5.

Another exemplary bulk reagent composition is substantially free of glycerol, has an inorganic salt concentration of 5 mM or less and has 0.1-0.4 mM and suitably about 0.375 mM of each of dATP, dGTP dCTP and about 0.182 mM dUTP or about 0.284 mM of dTTP, 0.02 µg/µl-0.40 ug/µL flap endonuclease, suitably about 0.035 µg/µl flap endonuclease, 0.1 U/µl to 0.2 U/µl, suitably, 0.146 U/µl polymerase, a bulking agent, suitably trehalose, at about 0.2 M to about 0.4 M, suitably about 0.3 M and a buffer, suitably MOPS buffer, suitably at a pH of about 7.5.

Another exemplary bulk reagent composition is substantially free of glycerol, has an inorganic salt concentration of 5 mM or less and has 0.1-0.4 mM and suitably about 0.375 mM of each of dATP, dGTP dCTP and about 0.182 mM dUTP or about 0.284 mM of dTTP and 0.02 µg/µl-0.40 ug/µL flap endonuclease, suitably about 0.03 µg/µl flap endonuclease. Some compositions include a bulking agent, suitably trehalose, at about 0.2 M to about 0.4 M, suitably about 0.3 M. Some compositions include a globular protein, suitably, bovine serum albumin (BSA), more suitably, ultrapure non-acetylated BSA. The globular protein can be present in an amount of 0.40 to 0.60 µg/µl, suitably, 0.50 µg/µl. Some compositions include a buffer, suitably Tris buffer, suitably at a pH of about 8.5.

Another exemplary bulk reagent composition is substantially free of glycerol, has an inorganic salt concentration of 5 mM or less and has 0.1-0.4 mM and suitably about 0.375 mM of each of dATP, dGTP dCTP and about 0.182 mM dUTP or about 0.284 mM of dTTP and 0.02 µg/µl-0.40 ug/µL flap endonuclease, suitably about 0.03 µg/µl flap endonuclease and 0.1 U/µl to 0.2 U/µl, suitably, 0.146 U/µl polymerase. Some compositions include a bulking agent, suitably trehalose, at about 0.2 M to about 0.4 M, suitably about 0.3 M. Some compositions include a globular protein, suitably, bovine serum albumin (BSA), more suitably, ultrapure non-acetylated BSA. The globular protein can be present in an amount of 0.40 to 0.60 µg/µl, suitably, 0.50 µg/µl. Some compositions include a buffer, suitably Tris buffer, suitably at a pH of about 8.5.

Another exemplary bulk reagent composition is substantially free of glycerol, has an inorganic salt concentration of 5 mM or less and has 0.1-0.4 mM and suitably 0.3 mM of each of dATP, dGTP dCTP and dUTP or dTTP and 0.02 µg/µl-0.40 ug/µL flap endonuclease, suitably about 0.03 µg/µl flap endonuclease and 0.1 U/µl to 0.2 U/µl, suitably, 0.146 U/µl polymerase, a bulking agent, suitably trehalose, at about 0.2 M to about 0.4 M, suitably about 0.3 M, a globular protein, suitably, bovine serum albumin (BSA), more suitably, ultrapure non-acetylated BSA, said globular protein being present in an amount of 0.40 to 0.60 µg/µl, suitably, 0.50 µg/µl, and a buffer, suitably Tris buffer, suitably at a pH of about 8.5.

Another exemplary bulk reagent composition is substantially free of glycerol, has an inorganic salt concentration of 5 mM or less and has 0.1-0.4 mM and suitably 0.375 mM of each of dATP, dGTP dCTP and dUTP or dTTP and 0.02 µg/µl-0.40 ug/µL flap endonuclease, suitably about 0.035 µg/µl flap endonuclease. In some compositions, the flap endonuclease is a Cleavase® enzyme. Some compositions include a bulking agent, suitably trehalose, at about 0.2 M to about 0.4 M, suitably about 0.36 M. Some compositions include a globular protein, suitably, bovine serum albumin (BSA), more suitably, ultrapure non-acetylated BSA. The globular protein can be present in an amount of 0.40 to 0.60 μg/μl, suitably, 0.50 μg/μl. Some compositions include a buffer, suitably MOPS buffer, suitably at a pH of about 7.5.

Another exemplary bulk reagent composition is substantially free of glycerol, has an inorganic salt concentration of 5 mM or less and has 0.1-0.4 mM and suitably 0.375 mM of each of dATP, dGTP dCTP and dUTP or dTTP and 0.02 μg/μl-0.40 ug/μL flap endonuclease, suitably about 0.035 μg/μl flap endonuclease and 0.1 U/μl to 0.2 U/μl, suitably, 0.167 U/μl polymerase. Some compositions include a bulking agent, suitably trehalose, at about 0.2 M to about 0.4 M, suitably about 0.36 M. Some compositions include a globular protein, suitably, bovine serum albumin (BSA), more suitably, ultrapure non-acetylated BSA. The globular protein can be present in an amount of 0.40 to 0.60 μg/μl, suitably, 0.50 μg/μl. Some compositions include a buffer, suitably MOPS buffer, suitably at a pH of about 7.5.

Another exemplary bulk reagent composition is substantially free of glycerol, has an inorganic salt concentration of 5 mM or less and has 0.1-0.4 mM and suitably 0.375 mM of each of dATP, dGTP dCTP and dUTP or dTTP and 0.02 μg/μl-0.40 ug/μL flap endonuclease, suitably about 0.035 μg/μl flap endonuclease and 0.1 U/μl to 0.2 U/μl, suitably, 0.167 U/μl polymerase, a bulking agent, suitably trehalose, at about 0.2 M to about 0.4 M, suitably about 0.36 M, a globular protein, suitably, bovine serum albumin (BSA), more suitably, ultrapure non-acetylated BSA, said globular protein being present in an amount of 0.40 to 0.60 μg/μl, suitably, 0.50 μg/μl, and a buffer, suitably MOPS buffer (such as 15 mM MOPS buffer), suitably at a pH of about 7.5.

Another exemplary bulk reagent composition is substantially free of glycerol, has an inorganic salt concentration of 5 mM or less and has 0.1-0.4 mM and suitably 0.375 mM of each of dATP, dGTP dCTP and dUTP or dTTP and 0.02 μg/μl-0.40 ug/μL flap endonuclease, suitably about 0.035 μg/μl flap endonuclease and 0.1 U/μl to 0.2 U/μl, suitably, 0.169 U/μl polymerase, a bulking agent, suitably trehalose, at about 0.2 M to about 0.4 M, suitably about 0.36 M, a globular protein, suitably, bovine serum albumin (BSA), more suitably, ultrapure non-acetylated BSA, said globular protein being present in an amount of 0.40 to 0.60 μg/μl, suitably, 0.51 μg/μl, a buffer, suitably MOPS buffer (such as 15 mM MOPS buffer), suitably at a pH of about 7.5 and a chelating agent, suitably EDTA at a concentration from about 0.05 to 0.2 mM, suitably, about 0.15 mM.

After formation of a bulk reagent composition it may be left at room temperature for a significant period before drying. The period can be for up to 8 hr before the drying step is initiated, or alternatively, for up to 1 hr, up to 2 hr, up to 4 hr, up to 6 hr, up to 10 hr, up to 12 hr, up to 14 hr, before the drying step is initiated. Inclusion of salts in the bulk reagent results in undesired hybridization products and other by-products during this incubation period. Such undesired hybridization and by-products are reduced or eliminated by forming the bulk reagent composition essentially without inorganic salt.

The presence of inorganic salts in a bulk reagent can result in one or more of the following undesirable properties. Nucleic acids may hybridize together, the hybridization being stimulated by the presence of inorganic salts such as potassium, sodium, manganese, magnesium and/or chloride. Also in the presence of inorganic salts like manganese and magnesium, undesirable enzyme activity can occur. As a result of nucleic acid hybridization and enzyme activity in the presence of salt, undesired side-products may start to form. Additionally, inorganic salts are hygroscopic and will draw moisture into a dried pellet. Rehydration of the dried pellet reduces storage stability, enzyme stability, and allows for additional spurious side product formation.

A dried pellet can contain regents to provide one single unit dose (SUD), or optionally, two or more SUDs. A single unit dose is a collection of regents necessary to perform a nucleic acid based assay on no more than a single sample. Single unit dose can refer to a liquid reagent or a dried pellet It is notable that a single unit dose, as referred to herein, need not contain all of the reagents necessary to perform a nucleic acid based assay on a single sample. A single unit dose may lack a reagent needed for performing nucleic acid based assay reactions. Similarly, a single unit dose may contain an insufficient amount of a reagent for performing nucleic acid based assay reactions. By way of example only, a dried single unit dose pellet may comprise adequate units of flap endonuclease for performing a nucleic acid based assay, but may contain no magnesium. In an example such as this, the magnesium can be added to the dried single unit dose pellet, such as by way of a reconstitution solution. Also by way of example only, a dried single unit dose may comprise an inadequate amount of dNTPs for performing a nucleic acid based assay. In an example such as this, the remainder of the dNTPs can be added to the dried single unit dose pellet, such as by way of a reconstitution solution. Ordinarily skilled artisans in possession of this disclosure will readily generate SUDs and dried pellet SUDs with varied compositions, as these examples are non-limiting.

In a preferred embodiment, bulk reagent comprises 5 mM or less of inorganic salt content, more preferably 4 mM or less of inorganic salt content, more preferably 3 mM or less of inorganic salt content, more preferably 2 mM or less of inorganic salt content, more preferably 1 mM or less of inorganic salt content, or more preferably 500 uM or less of inorganic salt content. Thus a preferred concentration range of inorganic salt in a bulk reagent is from about 5 mM to 0 mM inorganic salt content (inclusive of all whole and partial values therein). Common inorganic salts for a nucleic acid based assay reaction mixtures include one or more of sodium, potassium, manganese, magnesium and chloride, to name a few.

In one aspect, a bulk reagent comprises 5 mM or less of inorganic salt, the inorganic salts are present in a mass per microliter of 0.373 μg/μl or less, or 0.332 μg/μl or less, or 0.292 μg/μl or less. In a further aspect, a bulk reagent comprises 5 mM or less of inorganic salt, and the sodium chloride is present at a mass per microliter of 0.292 μg/μl or less, of 0.146 μg/μl or less, or of 0.0 μg/μl. In a further aspect, a bulk reagent comprises 5 mM or less of inorganic salt, and the sodium is present at a mass per microliter of 0.115 μg/μl or less, of 0.057 μg/μl or less, or of 0.0 μg/μl. In a further aspect, a bulk reagent comprises 5 mM or less of inorganic salt, and the potassium chloride is present at a mass per microliter of 0.373 μg/μl or less, of 0.186 μg/μl or less, or of 0.0 μg/μl. In a further aspect, a bulk reagent comprises 5 mM or less of inorganic salt, and the potassium is present at a mass per microliter of 0.196 μg/μl or less, of 0.098 μg/μl or less, or of 0.0 μg/μl. In a further aspect, a bulk reagent comprises 5 mM or less of inorganic salt, and the chloride is present at a mass per microliter of 0.355 μg/μl or less, of 0.178 μg/μl or less, of 0.089 μg/μl or less, or of 0.0 μg/μl. In a further aspect, a dried pellet is made from drying a liquid bulk reagent comprising 5 mM or less of an inorganic salt, and the percent mass of the inorganic salt to the mass of the pellet is 0.311% or less, 0.277% or less, or 0.244% or less. In a further aspect, there is provided a vessel that contains a dried single unit dose pellet with a percent mass of inorganic salt to mass of pellet of 0.311% or less, 0.277% or less, or 0.244% or less. In a further aspect, there is provided a multiwell plate comprising one or more wells, wherein each of the one or more wells contains a dried single unit dose pellet that contains a percent mass of inorganic salt to mass of pellet of 0.311% or less, 0.277% or less, or 0.244% or less.

In one aspect, a bulk reagent comprises 4 mM or less of inorganic salt, the inorganic salts are present in a mass per microliter of 0.298 µg/µl or less, or 0.266 µg/µl or less, or 0.234 µg/µl or less. In a further aspect, a bulk reagent comprises 4 mM or less of inorganic salt, and the sodium chloride is present at a mass per microliter of 0.234 µg/µl or less, of 0.117 µg/µl or less, or of 0.0 µg/µl. In a further aspect, a bulk reagent comprises 4 mM or less of inorganic salt, and the sodium is present at a mass per microliter of 0.092 µg/µl or less, of 0.046 µg/µl or less, or of 0.0 µg/µl. In a further aspect, a bulk reagent comprises 4 mM or less of inorganic salt, and the potassium chloride is present at a mass per microliter of 0.298 µg/µl or less, of 0.149 µg/µl or less, or of 0.0 µg/µl. In a further aspect, a bulk reagent comprises 4 mM or less of inorganic salt, and the potassium is present at a mass per microliter of 0.156 µg/µl or less, of 0.078 µg/µl or less, or of 0.0 µg/µl. In a further aspect, a bulk reagent comprises 4 mM or less of inorganic salt, and the chloride is present at a mass per microliter of 0.284 µg/µl or less, of 0.142 µg/µl or less, of 0.071 µg/µl or less, or of 0.0 µg/µl. In a further aspect, a dried pellet is made from drying a liquid bulk reagent comprising 4 mM or less of an inorganic salt, and the percent mass of the inorganic salt to the mass of the pellet is 0.249% or less, 0.222% or less, or 0.195% or less. In a further aspect, there is provided a vessel that contains a dried single unit dose pellet with a percent mass of inorganic salt to mass of pellet of 0.249% or less, 0.222% or less, or 0.195% or less. In a further aspect, there is provided a multiwell plate comprising one or more wells, wherein each of the one or more wells contains a dried single unit dose pellet that contains a percent mass of inorganic salt to mass of pellet of 0.249% or less, 0.222% or less, or 0.195% or less.

In one aspect, a bulk reagent comprises 3 mM or less of inorganic salt, the inorganic salts are present in a mass per microliter of 0.224 µg/µl or less, or 0.199 µg/µl or less, or 0.175 µg/µl or less. In a further aspect, a bulk reagent comprises 3 mM or less of inorganic salt, and the sodium chloride is present at a mass per microliter of 0.175 µg/µl or less, of 0.088 µg/µl or less, or of 0.0 µg/µl. In a further aspect, a bulk reagent comprises 3 mM or less of inorganic salt, and the sodium is present at a mass per microliter of 0.069 µg/µl or less, of 0.034 µg/µl or less, or of 0.0 µg/µl. In a further aspect, a bulk reagent comprises 3 mM or less of inorganic salt, and the potassium chloride is present at a mass per microliter of 0.224 µg/µl or less, of 0.112 µg/µl or less, or of 0.0 µg/µl. In a further aspect, a bulk reagent comprises 3 mM or less of inorganic salt, and the potassium is present at a mass per microliter of 0.117 µg/µl or less, of 0.059 µg/µl or less, or of 0.0 µg/µl. In a further aspect, a bulk reagent comprises 3 mM or less of inorganic salt, and the chloride is present at a mass per microliter of 0.213 µg/µl or less, of 0.107 µg/µl or less, of 0.053 µg/µl or less, or of 0.0 µg/µl. In a further aspect, a dried pellet is made from drying a liquid bulk reagent comprising 3 mM or less of an inorganic salt, and the percent mass of the inorganic salt to the mass of the pellet is 0.186% or less, 0.166% or less, or 0.146% or less. In a further aspect, there is provided a vessel that contains a dried single unit dose pellet with a percent mass of inorganic salt to mass of pellet of 0.186% or less, 0.166% or less, or 0.146% or less. In a further aspect, there is provided a multiwell plate comprising one or more wells, wherein each of the one or more wells contains a dried single unit dose pellet that contains a percent mass of inorganic salt to mass of pellet of 0.186% or less, 0.166% or less, or 0.146% or less.

In one aspect, a bulk reagent comprises 2 mM or less of inorganic salt, the inorganic salts are present in a mass per microliter of 0.149 µg/µl or less, or 0.133 µg/µl or less, or 0.117 µg/µl or less. In a further aspect, a bulk reagent comprises 2 mM or less of inorganic salt, and the sodium chloride is present at a mass per microliter of 0.117 µg/µl or less, of 0.058 µg/µl or less, or of 0.0 µg/µl. In a further aspect, a bulk reagent comprises 2 mM or less of inorganic salt, and the sodium is present at a mass per microliter of 0.046 µg/µl or less, of 0.023 µg/µl or less, or of 0.0 µg/µl. In a further aspect, a bulk reagent comprises 2 mM or less of inorganic salt, and the potassium chloride is present at a mass per microliter of 0.149 µg/µl or less, of 0.075 µg/µl or less, or of 0.0 µg/µl. In a further aspect, a bulk reagent comprises 2 mM or less of inorganic salt, and the potassium is present at a mass per microliter of 0.078 µg/µl or less, of 0.039 µg/µl or less, or of 0.0 µg/µl. In a further aspect, a bulk reagent comprises 2 mM or less of inorganic salt, and the chloride is present at a mass per microliter of 0.142 µg/µl or less, of 0.071 µg/µl or less, of 0.036 µg/µl or less, or of 0.0 µg/µl. In a further aspect, a dried pellet is made from drying a liquid bulk reagent comprising 2 mM or less of an inorganic salt, and the percent mass of the inorganic salt to the mass of the pellet is 0.124% or less, 0.111% or less, or 0.097% or less. In a further aspect, there is provided a vessel that contains a dried single unit dose pellet with a percent mass of inorganic salt to mass of pellet of 0.124% or less, 0.111% or less, or 0.097% or less. In a further aspect, there is provided a multiwell plate comprising one or more wells, wherein each of the one or more wells contains a dried single unit dose pellet that contains a percent mass of inorganic salt to mass of pellet of 0.124% or less, 0.111% or less, or 0.097% or less.

In one aspect, a bulk reagent comprises 1 mM or less of inorganic salt, the inorganic salts are present in a mass per microliter of 0.075 µg/µl or less, or 0.066 µg/µl or less, or 0.058 µg/µl or less. In a further aspect, a bulk reagent comprises 1 mM or less of inorganic salt, and the sodium chloride is present at a mass per microliter of 0.058 µg/µl or less, of 0.029 µg/µl or less, or of 0.0 µg/µl. In a further aspect, a bulk reagent comprises 1 mM or less of inorganic salt, and the sodium is present at a mass per microliter of 0.023 µg/µl or less, of 0.011 µg/µl or less, or of 0.0 µg/µl. In a further aspect, a bulk reagent comprises 1 mM or less of inorganic salt, and the potassium chloride is present at a mass per microliter of 0.075 µg/µl or less, of 0.037 µg/µl or less, or of 0.0 µg/µl. In a further aspect, a bulk reagent comprises 1 mM or less of inorganic salt, and the potassium is present at a mass per microliter of 0.039 µg/µl or less, of 0.020 µg/µl or less, or of 0.0 µg/µl. In a further aspect, a bulk reagent comprises 1 mM or less of inorganic salt, and the chloride is present at a mass per microliter of 0.071 µg/µl or less, of 0.036 µg/µl or less, of 0.018 µg/µl or less, or of 0.0 µg/µl. In a further aspect, a dried pellet is made from drying a liquid bulk reagent comprising 1 mM or less of an inorganic salt, and the percent mass of the inorganic salt to the mass of the pellet is 0.062% or less, 0.055% or less, or 0.049% or less. In a further aspect, there is provided a vessel that contains a dried single unit dose pellet with a percent mass of inorganic salt to mass of pellet of 0.062% or less, 0.055% or less, or 0.049% or less. In a further aspect, there is provided a multiwell plate comprising one or more wells, wherein each of the one or more wells contains a dried single unit dose pellet that contains a percent mass of inorganic salt to mass of pellet of 0.062% or less, 0.055% or less, or 0.049% or less.

In one aspect, a bulk reagent comprises 500 uM or less of inorganic salt, the inorganic salts are present in a mass per microliter of 0.037 µg/µl or less, or 0.033 µg/µl or less, or 0.029 µg/µl or less. In a further aspect, a bulk reagent comprises 500 uM or less of inorganic salt, and the sodium chloride is present at a mass per microliter of 0.029 µg/µl or less, of 0.015 µg/µl or less, or of 0.0 µg/µl. In a further aspect, a bulk reagent comprises 500 uM or less of inorganic salt, and the sodium is present at a mass per microliter of 0.011 µg/µl or less, of 0.006 µg/µl or less, or of 0.0 µg/µl. In a further aspect, a bulk reagent comprises 500 uM or less of inorganic salt, and the potassium chloride is present at a mass per microliter of 0.037 µg/µl or less, of 0.019 µg/µl or less, or of 0.0 µg/µl. In a further aspect, a bulk reagent comprises 500 uM or less of inorganic salt, and the potassium is present at a mass per microliter of 0.020 µg/µl or less, of 0.010 µg/µl or less, or of 0.0 µg/µl. In a further aspect, a bulk reagent comprises 500 uM or less of inorganic salt, and the chloride is present at a mass per microliter of 0.036 µg/µl or less, of 0.018 µg/µl or less, of 0.009 µg/µl or less, or of 0.0 µg/µl. In a further aspect, a dried pellet is made from drying a liquid bulk reagent comprising 500 uM or less of an inorganic salt, and the percent mass of the inorganic salt to the mass of the pellet is 0.031% or less, 0.028% or less, or 0.024% or less. In a further aspect, there is provided a vessel that contains a dried single unit dose pellet with a percent mass of inorganic salt to mass of pellet of 0.031% or less, 0.028% or less, or 0.024% or less. In a further aspect, there is provided a multiwell plate comprising one or more wells, wherein each of the one or more wells contains a dried single unit dose pellet that contains a percent mass of inorganic salt to mass of pellet of 0.031% or less, 0.028% or less, or 0.024% or less.

In one aspect, a bulk reagent comprises from about 5 mM to about 500 uM of inorganic salt, the inorganic salts are present in a mass per microliter from about 0.373 µg/µl to about 0.029 µg/µl. In a further aspect, a bulk reagent from about 5 mM to about 500 uM of inorganic salt, and the sodium chloride is present at a mass per microliter 0.292 µg/µl to about 0.029 µg/µl. In a further aspect, a bulk reagent from about 5 mM to about 500 uM of inorganic salt, and the sodium is present at a mass per microliter 0.115 µg/µl to about 0.006 µg/µl. In a further aspect, a bulk reagent comprises from about 5 mM to about 500 uM of inorganic salt, and the potassium chloride is present at a mass per microliter from about 0.373 µg/µl to about 0.019 µg/µl. In a further aspect, a bulk reagent from about 5 mM to about 500 uM of inorganic salt, and the potassium is present at a mass per microliter 0.196 µg/µl to about 0.010 µg/µl. In a further aspect, a bulk reagent from about 5 mM to about 500 uM of inorganic salt, and the chloride is present at a mass per microliter 0.355 µg/µl to about 0.009 µg/µl. In a further aspect, a bulk reagent comprises from about 5 mM to about 500 uM of inorganic salt, the inorganic salts are present in a mass per microliter from about 0.373 µg/µl to about 0.029 µg/µl, and the sodium chloride is present at a mass per microliter of about 0 µg/µl. In a further aspect, a bulk reagent comprises from about 5 mM to about 500 uM of inorganic salt, the inorganic salts are present in a mass per microliter from about 0.373 µg/µl to about 0.029 µg/µl, and the potassium chloride is present at a mass per microliter of about 0 µg/µl. In a further aspect, a dried pellet is made from drying a liquid bulk reagent comprising from 5 mM to 500 uM of an inorganic salt, and the percent mass of the inorganic salt to the mass of the pellet is from about 0.311% to 0.024%. In a further aspect, a dried pellet is made from drying a liquid bulk reagent comprising from 5 mM to 500 uM of an inorganic salt, and the percent mass of the inorganic salt to the mass of the pellet is from about 0.311% to 0.024%, and the percent mass of the sodium chloride to mass of the pellet is about 0%, or the percent mass of the potassium chloride to mass of the pellet is about 0%. In a further aspect, there is provided a vessel that contains a dried single unit dose pellet with a percent mass of inorganic salt to mass of pellet is from about 0.311% to 0.024%, and the percent mass of the sodium chloride to mass of the pellet is about 0% or the percent mass of the potassium chloride to mass of the pellet is about 0%. In a further aspect, there is provided a multiwell plate comprising one or more wells, wherein each of the one or more wells contains a dried single unit dose pellet that contains a percent mass of inorganic salt to mass of pellet is from about 0.311% to 0.024%, and the percent mass of the sodium chloride to mass of the pellet is about 0% or the percent mass of the potassium chloride to mass of the pellet is about 0%.

In one embodiment there is provided a multiwell plate comprising one or more wells. In one aspect, one or more wells comprise walls that are constructed from a material comprising a low moisture-vapor transmission rate, thermal conductivity, optical transparency, low autofluorescence, or a combination thereof. In one aspect, a one or more wells comprise walls that are cone shaped. In one aspect, the wells comprise walls configured to fit into a thermally conductive tube receiving area of a device for performing a nucleic acid based assay reaction. In one aspect, one or more wells of the multiwell plate comprise an opening for access to the chamber of the well. In one aspect, one or more wells each comprises a cap to seal the opening of the associated well. In one aspect, an opening of each of the one or more wells is sealed with a cap that is a low moisture-vapor transmission rate foil. In one aspect, an opening of each of the one or more wells is sealed with a cap that is a low moisture-vapor transmission rate elastomeric substance. In one aspect, a multiwell plate comprises one or more wells as described herein, and wherein a chamber of the well contains a dried single unit dose pellet comprising a flap endonuclease and an inorganic salt, wherein the percent mass of the inorganic salt to the mass of the pellet is from about 0.311% to 0.024%.

III. Equipment and Methods for Drying

Bulk reagents can be lyophilized using standard methods and equipment. Freeze driers are available from, e.g., GEA Process Engineering, Columbia, MD. Contract freeze drying services are provided by, e.g., Biopharma Technology Ltd., Winchester, Hampshire, Great Britain and by BioPharma Solutions Sterile Contract Manufacturing, Baxter Healthcare Corp, Deerfield, IL. Guidance for lyophilization is available from, e.g., L. Rey, J. C. May (eds.) (2010) Freeze Drying/Lyophilization of Pharmaceuticals and Biological Products, $3^{rd}$. ed. Informa Healthcare, NY or Methods in Enzymology, Vol. 22, Pages 33-39, Academic Press, New York (1971); or Freeze-Drying, E. W. Flosdorf, Rheinhold, New York (1949). Optionally, oxygen content can be reduced during freeze-drying (Phillips et al (2001) Biologics. 19:219).

A variety of containers are suitable for drying. A container should be able to withstand the outside pressure when the container is sealed and stored under partial vacuum. The container should be made of a material that allows a reasonable transfer of heat from outside to inside. The size of the container is preferably such that the solution to be dried occupies not more than 20% of the total volume to avoid overflow.

Samples can be dried in separate vessels or in multi-specimen vessels. A multi-specimen vessel means a contiguous vessel that can contain at least two specimens such that they can be stored and manipulated in parallel but separately. Standard formats for multi-specimen receptacles include 6, 24, 96, 384 or 1536 wells. The volume of each well in an example of a 96 well format is about 300-400 microliters with a working volume of about 75-200 microliters. Volumes generally vary inversely with the number of wells, typically in a range between 1 nL and 10 mL for each well, although other sizes are also contemplated. Exemplary wells can have flat bottoms, round bottoms, or V-shaped bottoms among others. As used herein, a vessel is also referred to as a well. As used herein, a multi-specimen vessel is also referred to as a multiwell plate. In addition, wells are sometimes further referred to as reaction wells. The term reaction well does not require that any reaction actually take place in the reaction well. Rather, the term is used to refer to a vessel or well that contains a reagent, and that may have no reaction therein, a partial reaction therein, or a full reaction therein.

A multiwell plate, in some embodiments herein, can undergo lyophilization to form a dried composition from an aqueous solution. Lyophilization may occur in a nest device (see application U.S. Provisional Application No. 62/200,370). A nest is a container for the cartridge with vents which can be closed by a mechanism operable from outside a sealed lyophilization chamber. The nest containing the multiwell plate is placed within a lyophilization chamber with the one or more vents in the open position. The chamber is then sealed and a lyophilization atmosphere is applied throughout the chamber including the space within the nest. The one or more vents are then closed, thereby sealing the nest. The seal on the lyophilization chamber is later released and the nest containing the multiwell plate is removed. The nest may then be relocated and stored with the multiwell plate positioned therein until an operator is ready to use the lyophilized composition located therein or to reseal the multiwell plate containing the lyophilized specimens for further storage or sale. The wells of the multiwell plate can then be sealed substantially inhibiting entry of moisture from ambient air. The small amount of moisture entry into a sealed multiwell plate can be prevented by storing the sealed multiwell plate in a pouch containing desiccant. Similarly, separate vessels can undergo lyophilization, and can undergo lyophilization in a nest.

Other drying methods include spray drying, fluidized bed drying, dehumidifiers, and batch contact drying where a filter cake is dried at low temperature under vacuum to a free flowing dry product (NP Cheremisinoff (2000) Handbook of Chemical Processing Equipment, Butterworth Heinemann, Boston, MA). Dehumidifies are available from Bry Air, Inc., Sunbury, Ohio, and DST Seibu Giken, Wyomissing, PA Rotary dryers, conical dryers, and shelf dryers are available (McGill AirPressure LLC, Columbus, Ohio). In one embodiment, vacuum dryers remove moisture by exposing the materials to reduced pressure, where just enough heat is used to replace that lost through vaporization. Desiccants include silica gel desiccants, molecular sieve desiccants such as aluminosilicate and synthetic zeolite, and bentonite desiccants.

Reaction mixtures are preferably dried in the same vessel as that in which they will be reconstituted for use.

A lyophilized or otherwise dried formulation has a low water content, for example, under 5% water by weight, under 4%, under 3%, under 2%, under 1.0%, under 0.5%, under 0.2%, under 0.1%, under 0.05%, under 0.02%, under 0.01% by weight, and so on.

IV. Storage

Lyophilized or otherwise dried compositions are subject to storage before use. The period of storage can include a period of time in which the dried compositions are stored at room temperature exposed to ambient air. Such a period can be up to 3 hours, or alternatively, for up to 1.0 hour, up to 1.5 hours, up to 2.0 hours, up to 2.5 hours or ranges of any of the times, such as from 1 minute to 180 minutes, or from 1 minute to 100 minutes, or from 1 minute to 60 minutes, or from 1 minute to 30 minutes or from 1 minute to 20 minutes, or from 1 minute to 10 minutes. The absolute humidity during such storage can be at least 2.3 g water per cubic meter of air at 30 degrees C., or alternatively, greater than 1.8, 2.0, 2.2, 2.4, 2.6, 2.8, 3.0 grams of water per cubic meter of air at 30 degrees C.

Storage can also include a longer period in which dried compositions are sealed substantially preventing contact with ambient air outside the seal. This period of storage can be for a long time, for example, at least a week, at least a month, at least six months, at least a year or at least two years. A period from one month to two years is exemplary.

Ranges of storage temperatures, for long-term storage or for long or short-term stability studies include, e.g., 0-2 degrees C., 0-4 degrees C., 2-4 degrees C., 2-6 degrees C., 20 degrees C., 25 degrees C., 30 degrees C., 40 degrees C., 50 degrees C., 60 degrees C., as well as subzero temperatures such as −4 to −2 degrees C., −6 to −2 degrees C., −8 to −2 degrees C., −10 to −2 degrees C., −20 degrees C., −40 degrees C., −60 degrees C., −80 degrees C., under liquid nitrogen. Preferably, storage is above freezing point and in the range of about 4-8 degrees C. Accelerated degradation studies can be conducted at about 25 degrees C., about 30 degrees C., about 35 degrees C., about 40 degrees C., for a period of, for example, one hour, two hours, four hours, 24 hours, two days, four days, eight days, one month, and so on. Conditions for storage or, alternatively, for stability testing, can be those that fluctuate in temperature, such as those that fluctuate from above to below a freezing point.

The essential absence of inorganic salts reduces loss of enzyme activity and formation of by-products during storage of bulk reagents before drying, during short term storage of dried composition before sealing, and long term storage after sealing. Preferably enzyme activity after all storage is at least 99% the value before immediately prior to initiating storage, at least 98%, at least 95%, at least 90%, at least 80%, at least 75%, at least 70%, at least 60%, at least 50%, at least 40%, at least 30%, at least 20%, and ranges bordered by these percentages, of the value prior to initiating storage, or alternatively, to the value of a comparator sample stored under optimal conditions.

V. Reconstitution

A preferred reconstitution solution provides about 3.0 to about 12.0 mM $MgCl_2$, and about 0 to about 80 mM KCl in water. The reconstitution solution can also contain about 0.012 to about 0.020% (w/v) methyl paraben, about 0.006 to about 0.010% (w/v) propyl paraben, and/or about 0.25 to about 0.35% (v/v) absolute ethanol among other components.

Reconstitution time can be, under 1 sec, under 2 sec, under 5 sec, under 10 sec, under 15 sec, under 20 sec, under 50 sec, or under 60 sec (1 minute), after aqueous solution suitable for intended use of the dried composition is contacted with the dried composition, with contact optionally facilitated by any of shaking, tapping vortexing, rocking, drawing in and out of a pipet tip, or folding or squeezing of a malleable vial. An exemplary reconstitution time is 2-10 sec. Reconstitution time can be measured with the reconstitution solution at any of refrigerator temperature (about 4 degrees C.), ambient temperature solution about 23 degrees C., or with a warm solution at about 37 degrees C. Typically, the dried composition has been removed from a refrigerator and is cold before addition of the reconstitution solution. The environment (the room) for any of these procedures is typically ambient temperature or about 23 degrees C. The time at which a substance is determined to be reconstituted can be, for example, the time at which the substance is determined to be completely solubilized. Complete solubilization can be determined by visual inspection, for example, where absence of turbidity or absence of a schlieren pattern is a measure of complete solubilization. Alternatively, complete solubilization can be determined by way of an optical instrument, such as a machine that measures light scattering.

VI. Stability of Compositions

Stability of compositions is typically assessed after reconstitution of a dried product by determining the activity (i.e., rate or yield of detection) or formation of by-products that occurred in the composition. Lack of stability can result from loss of activity or formation of by-products during storage either before or after drying. Activity or formation of by-products can be absolute or relative measures. If relative, the base line for comparison can be a bulk reagent mixture before drying and reconstitution or a control reconstituted mixture differing from that under test in a defined way (e.g., presence of $Mg^{2+}$ or other salt). Activity can be assessed by rate of real time cleavage or amplification or final yield of cleavage or amplification product or hit rate. Side products can be assayed by one or more of gel electrophoresis, a gel scanner, agarose gels, capillary electrophoresis, and so on.

The activity of a reconstituted amplification mixture (corrected if necessary for any differences due to a different volume of reconstitution) is preferably within 75, 80, 85, 90, or 95% or is indistinguishable within experimental error from that of the bulk reagent before drying. The side products present within a reconstituted amplification mixture (corrected if necessary for any differences due to a different volume of reconstitution) are preferably less than 20, 15, 10, 5, 4, 3, 2 or 1% by weight or average moles of the original compounds present in the bulk reagent before drying. Sometimes side products are below a limit of detection.

VII. Kits

The dried compositions described above can be provided in a kit. Such a kit can contain the dried compositions in a vessel, such as a tube. In some embodiments, the kit contains a multiwell plate comprising one or more wells. Some kits contain a plurality of dried compositions supplied in separate vessels. Some kits include one or more multiwell plates including multiple dried compositions in one or more sealed well members of the multiwell plates.

Some kits also include a reconstitution solution in a separate vessel from dried compositions. The reconstitution solution can be provided in bulk for dispensing aliquots into individual dried composition vessels or can be provided in the form of one or more unit dosages, each for combination with a single vessel containing a dried composition.

Optionally a vessel containing dried composition and a vessel containing reconstitution solution can be separated by a frangible material. The frangible material can be aluminium foil, polypropylene, polyester, polyvinylchloride (PVC), polyethylene. The barrier can include one, two, three or more layers, each layer having the same composition, or each layer having a different composition, such as a foil layer in contact with a PVC layer. Films can be acquired from, e.g., Dow Chemical Co., Midland, MI or Arkema, Inc., King of Prussia, PA Piercing of the frangible material allows the reconstitution solution to contact the lyophilized composition The kit can be designed to fit into a thermocycler or into an incubator so that enzymatic reactions take place directly in a compartment of the kit to avoid need to transfer compositions to different reaction vessel or containers holding such vessels.

Kits can be adapted for introduction of a user-supplied reagent into a vessel within the kit, for example, by way of a port, a hose, a syringe puncturing a septum (see, US2014/0121515 and US2014/0276356), or alternatively, the user-supplier reagents, such as a nucleic acid template, can be mixed with reagents of the disclosure in a user-supplied container. One or more of the compartments of the kit can be supplied in an empty state and used as a mixing chamber.

VIII. Dialysis of Flap Endonucleases

Some enzymes for use in the present disclosure are manufactured in a glycerol containing buffer. Glycerol content can impair lyophilization. It is therefore necessary to prepare solutions containing glycerol-free enzyme solutions and substantially no inorganic salts by dialysing the enzyme into a glycerol-free buffer. This dialysis can be used to substantially remove the glycerol and replaces it with buffer. The dialyzed enzyme can then be used to prepare a glycerol-free lyophilization formulation with substantially no inorganic salts. Accordingly, there is also disclosed herein a dialysis composition comprising, consisting or consisting essentially of an aqueous solution containing an organic buffer, a bulking agent, chloride ions and a chelating agent. The bulking agent can be trehalose. The bulking agent can be present at a concentration from about 100 mM to 300 mM, suitably, 200 mM. The organic buffer can be tris (hydroxymethyl)aminomethane (Tris) buffer. The Tris buffer can be present at a concentration of from 10 mM to 30 mM, suitably at a concentration of 50 mM. The chloride ions can be KCl. The chloride ions can be present at a concentration of about 40 to 60 mM, suitably, 50 mM. The chelating agent can be EDTA. The chelating agent can be present in the aqueous solution at a concentration from 0.05 to 0.2 mM, suitably, 0.1 mM. The dialysis composition can comprise a flap endonuclease.

An exemplary dialysis composition is an aqueous solution comprising, consisting or consisting essentially of Tris buffer (pH 8.0), trehalose, KCl and EDTA.

Another exemplary dialysis composition is an aqueous solution comprising, consisting or consisting essentially of about 20 mM Tris buffer (pH 8.0), about 200 mM trehalose, about 50 mM KCl and about 0.1 mM EDTA.

A method for preparing a substantially glycerol-free flap endonuclease composition is also disclosed in which the flap endonuclease and glycerol is dialysed to obtain a substantially glycerol-free flap endonuclease composition. Suitably, the glycerol is present in an amount from about 0 to about 0.35% (w/v) glycerol, suitably, from about 0 to about 0.2% (w/v) glycerol, suitably, about 0.1% (w/v) glycerol, suitably, about 0.01% (w/v) glycerol.

EXAMPLES

Example 1 Bulk Reagents

Examples 1 to 3 illustrate making a bulk reagent, drying a single unit dose (SUD) volume of the bulk reagent to get a SUD dried pellet in a vessel, and reconstituting the dried pellet to get an SUD amplification and detection mixture. Table 1 and Table 2 disclose components of exemplary bulk reagents for drying. The two tables also disclose exemplary single unit dose concentrations. Master mix 1 was a 2× master mix comprising 0.4 mM of each of dATP, dGTP, dCTP and dTTP; 0.8 mM dUTP; BSA, and substantially no inorganic salts. Taq polymerase in Table 1 was in a glycerol free Tris buffer containing a cationic detergent. 2× Master Mix 2 is: 0.4 mM dATP, dGTP, dCTP, 0.8 mM dUTP, 0.74 U/uL GoTaq® MDx Hot Start polymerase, glycerol free in proprietary buffer containing Tris and non-acetylated BSA, 0.48 M trehalose. 50× GoScript RT Mix is as follows: 20 U/μL GoScript®, 8 Units/μL RNasin® Plus RNase Inhibitor in Table 2; 10 U/μL GoScript®, 8 Units/μL RNasin™ Plus in Table 1.

GoScript® RT Custom is a concentrated solution of GoScript RT at 160 U/uL, glycerol free, no RNase inhibitor. Stabilizers that can be included deamidation inhibitors, anti-oxidants, detergents, and surfactants, such as the surfactants: fatty acid esters of sorbitan polyethoxylates (e.g., polysorbate 20 or polysorbate 80), and poloxamer 188.

TABLE 1

Exemplary Bulk Reagent for Drying

| Description | Bulk Reagent (concentration with appropriate units) | Quantity per Liter | SUD (concentration with appropriate units) | Workable range (concentration with appropriate units) |
|---|---|---|---|---|
| 1.4M Trehalose | 0.30M | 214 mL | 0.24M | 0.16-0.32M |
| Soln, EDTA 0.5M pH 8.0 | 2.19 mM | 4.4 mL | 1.75 mM | 0.0-3.5 mM |
| 2X Master Mix 1, w/o salt, w/o MgCl$_2$ | 1.25X | 625 mL | 1X | |
| Taq polymerase (50 U/μl) | 0.4 U/μL | 400 kU (8.00 mL) | 0.32 U/μL | 0.1-1.0 U/μl |
| 50X GoScript™ RT Mix for 1-Step RT-qPCR, Low Glycerol, Custom | 1.25X | 25.0 mL | 1X | |
| GoScript™ RT Custom Formulation, 160 U/μL | 0.25 U/μL | 250 kU (1.6 mL) | 0.20 U/μL | 0.1-0.6 U/μl |
| 10X oligonucleotide mix | 1.25X | 125 mL | 1X | 0.7X-1.3X |

TABLE 2

Exemplary Bulk Reagent for Drying

| Description | Bulk Reagent (concentration with appropriate units) | Quantity per Liter | SUD (concentration with appropriate units) | Workable range (concentration with appropriate units) |
|---|---|---|---|---|
| Solution EDTA 0.5M pH 8.0 | 2.19 mM | 4.38 mL | 1.75 mM | 0.0-3.5 mM |
| 2X Master Mix 2, w/o salt, w/o MgCl$_2$, w/extra Taq Pol, w/trehalose, w/nucleotides | 1.25X | 625 mL | 1X | |
| from trehalose | 0.30M | " | 0.24M | 0.16-0.32M |
| From Taq Pol | 0.46 U/μL | " | 0.37 U/μL | 0.1-1.0 U/μl |
| 50X GoScript™ RT Mix for 1-Step RT-qPCR, Low Glycerol, Custom, w/RNasin Plus | 1.25X | 25.0 mL | 1X | |
| From RT | 0.5 U/μL | " | 0.4 U/μL | 0.1-0.6 U/μl |
| 10X oligonucleotide mix | 1.25X | 125 mL | 1X | 0.7X-1.3X |

TABLE 3

Exemplary Bulk Reagent for Drying

| Description | Stock Concentration | End Concentration | Final Vol |
|---|---|---|---|
| AllStart 2X Master Mix (without KCL and withoutMgCl$_2$) | 2X | 1X | 12 µl/reaction |
| 10X PnP Mix | 10X | 1X | 2.5 µl/reaction |
| Z05 DNA Polymerase | 200 U/µl | 4 U/µl | 1 µl/50 µl reaction mix volume |
| AMV Reverse Transcriptase | 80 U/µl | 5 U/µl | 3.13 µl/50 µl reaction mix volume |
| T4G32P (protein for unfolding nucleic acids) | 10 U/µl | 2.5 U/µl | 12.50 µl/50 µl reaction mix volume |
| Enzyme Dilution Buffer | | | 33.4 µl/50 µl reaction mix volume |
| 10X oligonucleotide mix | 10X | 1.25X | 1X |

The 10× oligonucleotide mix in each of the bulk amplification reagents for Tables 1 to 3 included collections of primers and probes for performing amplification and detection reactions in the below examples. Ordinarily skilled artisans will understand how to prepare primer and probe mixtures for an amplification reaction (see e.g., Innis, Michael A. et al., PCR Protocols: A Guide to Methods and Applications, Academic Press (1990)). For the below examples, primers and probes were present in the bulk reagent at concentrations from about 8 uM to about 12 uM.

Example 2. Lyophilization

In this example, the bulk reaction mixtures were dried using a lyophilizer. 24 microliters of bulk amplification reagents described generally in example 1 was added to a vessel and then loaded into a lyophilization chamber. For the examples herein, 24 ul represents the amount of bulk reagent used to perform an amplification and detection reaction on a single sample (also referred to as a single unit dose or an SUD). In this example, a multiwell plate (specifically a 12-well plate) was used for both the lyophilization reaction and for storage of the lyophilized (dried) pellet present in the wells of the multiwell plate. Each of the 12 wells of the 12-well plate received a 24 ul aliquot of the bulk reaction mixture. A lyophilization cycle was turned on (about 36 hour run). Following the lyophilization cycle, the 12-well plate was retrieved and transferred to a location where the individual vessels of the 12-well plate were sealed. Vessels were sealed with a metallic foil over the vessel opening. The metallic foil was a low moisture-vapor transmission rate foil. The sealed 12-well plates were then pouched with a desiccant.

Example 3. Reconstitution Solution

This example describes one reconstitution solution. The purpose of the reconstitution solution is to rehydrate the dried pellet in preparation for using the reconstituted pellet to perform detection nucleic acid based reaction on a sample. To each of the 12-wells of the 12-well plate from example 2, 24 ul of reconstitution solution was dispensed by pre-piercing the foil cover on the well and then dispensing the reconstitution solution into the well. Table 4 discloses the reconstitution solution used in these examples, providing both bulk reconstitution solution concentrations and final assay concentrations. Following reconstitution of the dried pellet, target nucleic acids from a sample were added to the wells and a PCR amplification and detection reaction was performed.

TABLE 4

Universal Reconstitution Solution

| Description | Formula weight | Bulk Recon Soln, (concentration with appropriate units) | Quantity per Liter | Final Assay Solution (concentration with appropriate units) |
|---|---|---|---|---|
| MgCl$_2$ | 1.00M liq Stk | 5.19 mM | 5.19 mls | 4.15 mM |
| KCl | 74.55 g | 81.3 mM | 6.06 | 65 mM |
| Methyl Paraben | 152.15 g/mol | 0.02% w/v | 0.20 g | .016% |
| Propyl Paraben | 180.2 g/mol | 0.01% w/v | 0.10 g | .008% |
| Ethyl Alcohol, Absolute | 46.07 g/mol | 0.33% v/v | 3.30 mL | 0.26% |

Example 4. Negative Influence of Inorganic Salts on Dried Bulk Reagent

This example describes the negative influence that the presence of inorganic salts in the bulk reagents has on the dried pellet. Two bulk reagent mixtures were prepared generally according to example 1 and Table 5. The difference between Bulk Reagent A and Bulk Reagent B in Table 5 was the presence or absence of MgCl$_2$ in the reaction mixtures.

TABLE 5

Bulk Reagents with and without inorganic salts

| | Bulk Reagent A (without MgCl$_2$ and without KCl) | Bulk Reagent B (with MgCl$_2$ and without KCl) |
|---|---|---|
| Trehalose | 0.30M | 0.30M |
| Hot Start Taq DNA Polymerase (glycerol free) | 0.46 Units per microliter | 0.46 Units per microliter |
| Reverse Transcriptase | 0.5 Units per microliter | 0.5 Units per microliter |
| RNasin | 0.2 Units per microliter | 0.2 Units per microliter |
| dNTP mix | 0.25 mM dNTP, 0.5 mM UTP | 0.25 mM dNTP, 0.5 mM UTP |
| Nucleic Acids§ | 7 micromolar (uM) | 7 micromolar (uM) |
| KCl | 0 mM | 0 mM |
| MgCl$_2$ | 0 mM | 2.5 mM |
| Low Glycerol Buffer | 2.7 mM Na$^+$ | 2.7 mM Na$^+$ |
| | 0.035 mM K$^+$ | 0.035 mM K$^+$ |

§Nucleic Acids were a multiplex primer and probe mix made up of the following primer probe sets: for amplification and detection of influenza A there were 2 forward primers, 3 reverse primers, and 3 probes (two different flu A target regions); for influenza B there were 1 forward primers, 1 reverse primer, and 1 probe; for RSV there were 1 forward primers, 1 reverse primer, and 1 probe for RSVA and there were 1 forward primers, 1 reverse primer, and 1 probe for RSVB; and for the internal control there were 1 forward primers, 1 reverse primer, and 1 probe. The value of 7 micromolar is the sum of all primer concentrations wherein each primer is about 400 nM.

Each of liquid bulk reagents A and B were prepared on ice. Bulk reagents A and B were then each separately aliquoted into the wells of a number of multiwell plates (specifically here, 12-well plates were used). These 12-well plates containing either 12 aliquots of bulk reagent A or 12 aliquots of bulk reagent B were then separated into four different incubation conditions: (1) 90 minute incubation on ice; (2) 90 minute incubation at room temperature; (3) 180 minute incubation on ice; or (4) 180 minute incubation at room temperature. Thus, one portion of each bulk reagent mixture was incubated at room temperature for 180 minutes and the other portion was incubated on ice for 180 minutes. Likewise, one portion of each bulk reagent mixture was incubated at room temperature for 90 minutes and the other portion was incubated on ice for 90 minutes. In all cases, addition of the nucleic acid component to the reaction mixture (added as the final component) indicated the start of the incubation times.

Following the incubation times, the aliquoted bulk reagents in the 12-well plates were then lyophilized until substantially dry compositions were obtained. Each of the resulting dried compositions in a well of the 12-well plates represented a dried single unit dose for a triplex amplification and detection reaction to identify one or more of influenza A, influenza B and respiratory syncytial virus B in a sample.

The dried compositions were reconstituted with a reconstitution solution containing 65 mM of KCl, methyl and propyl paraben at 0.02% w/v and 0.01% w/v, respectively, and 0.33% v/v ethyl alcohol absolute. The reconstitution solution for dried compositions made from bulk reagent A also contained 2.5 mM MgCl$_2$.

All three of influenza A, influenza B, and respiratory syncytial virus B positive samples were combined into the reconstituted reaction mixtures at 3 times their LoD, such that all components of the reconstituted mix were at about 80% of their bulk reagent concentration. These positive samples were extracted viruses in a negative plasma combined with a transport medium and serially diluted to the desired concentration (with the exception that the RSVB sample serial dilution was off by a factor of 10). As indicated in Table 6, the primers and probe mix was designed to specifically detect each of the three viral targets, namely influenza A, influenza B, or respiratory syncytial virus type B, in a separate fluorescent channel, albeit in a single molecular reaction.

The samples were assayed using a real-time PCR compatible thermal cycler (ABI 7500FAST, Applied Biosystems, Carlsbad, CA). Results are presented in Table 6. The percent positive value in the table represents the number of samples that had RFU values that exceeded the threshold value as a percentage of the 12 samples tested. The amount of virus (viral particles per assay) was an amount sufficient to give at least a 95% positive compared to the positive control.

TABLE 6

| | Results | | |
|---|---|---|---|
| Condition | Influenza A Avg RFU For Positive Samples No. Positive/ % Positive | Influenza B Avg RFU For Positive Samples No. Positive/ % Positive | RSVB Avg RFU For Positive Samples No. Positive/ % Positive |
| #1 Bulk Reagent B 90 min Incubation On Ice | 602,587 6 of 12/50% | 303,112 11 of 12/92% | 320,017 12 of 12/100% |
| #2 Bulk Reagent A 90 min Incubation On Ice | 1,235,701 12 of 12/100% | 1,028,348 12 of 12/100% | 1,107,497 12 of 12/100% |
| #3 Bulk Reagent B 90 min Incubation Room Temp | 163,536 4 of 12/33% | 94,229 11 of 12/92% | 684,384 12 of 12/100% |

TABLE 6-continued

| | Results | | |
|---|---|---|---|
| Condition | Influenza A<br>Avg RFU For<br>Positive Samples<br>No. Positive/<br>% Positive | Influenza B<br>Avg RFU For<br>Positive Samples<br>No. Positive/<br>% Positive | RSVB<br>Avg RFU For<br>Positive Samples<br>No. Positive/<br>% Positive |
| #4 Bulk Reagent A<br>90 min Incubation<br>Room Temp | 1,699,434<br>12 of 12/100% | 1,832,464<br>12 of 12/100% | 1,064,536<br>12 of 12/100% |
| #5 Bulk Reagent B<br>180 min Incubation<br>On Ice | 576,226<br>12 of 12/100% | 530,568<br>12 of 12/100% | 1,048,669<br>12 of 12/100% |
| #6 Bulk Reagent A<br>180 min Incubation<br>On Ice | 1,396,077<br>12 of 12/100% | 1,314,236<br>12 of 12/100% | 934,325<br>12 of 12/100% |
| #7 Bulk Reagent B<br>180 min Incubation<br>Room Temp | 34,092<br>(below RLU threshold)<br>0 of 12/0% | 57,484<br>3 of 12/25% | 394,945<br>12 of 12/100% |
| #8 Bulk Reagent A<br>180 min Incubation<br>Room Temp | 1,970,034<br>12 of 12/100% | 1,896,883<br>12 of 12/100% | 1,074,004<br>12 of 12/100% |

These results indicate that bulk reagents (prelyophilization solutions without $MgCl_2$ and KCl) are stable for at least 180 minutes at room temperature. Dried SUD pellets from bulk reagent A, once reconstituted and combined with samples, provided amplification and detection reactions that were more robust than those provided by dried SUD pellets from bulk reagent B. Bulk reagent B, when incubated at room temperature or even on ice for as few as 90 minutes, then dried and reconstituted to generate an amplification reaction mixture, provided an amplification reaction with a relatively lower signal and with an abundance of small side products compared to bulk reagent A under the same conditions. Bulk reagents containing little to no inorganic salts are useful for drying to generate a dried composition containing components for an amplification reaction, including polymerase enzyme components, dNTPs and nucleic acids.

Example 5. Stability of Dried Pellets, with or without Salts

This example compares the stability of single unit dose dried pellets containing salts with single unit dose dried pellets containing no salts (less than 6 mM inorganic salt). The single unit dose pellets were made by drying a bulk reagent generally as described in Table 5 above Immediately after synthesis, bulk reagent A and bulk reagent B were each aliquoted into separate multiwell reaction plates (12-well) and dried using a lyophilizer. Following lyophilization, the multiwell plates containing dried pellets were placed in a nitrogen gas environment having a relative humidity of about 5%, and the multiwell plates were sealed by covering the well openings with a foil. Sealed plates were placed into an aluminium pouch containing a desiccant, and the pouches were then sealed. The sealed pouches containing the dried pellets in multiwell plates were stored for eight days at 4 degrees C.

Following the eighth day, the pouched multiwell plates were transferred into one of three conditions as follows: Condition #1-1 subset of pouched multiwell plates containing dried pellets from bulk reagent A and 1 subset of pouched multiwell plates containing dried pellets from bulk reagent B were removed from the pouch and placed in a 15 degrees C. environment with 70% relative humidity; Condition #2-1 subset of pouched multiwell plates containing dried pellets from bulk reagent A and 1 subset of pouched multiwell plates containing dried pellets from bulk reagent B were removed from the pouch and placed in a 45 degrees C. environment with 15% relative humidity (accelerated stability); and Condition #3-1 subset of pouched multiwell plates containing dried pellets from bulk reagent A and 1 subset of pouched multiwell plates containing dried pellets from bulk reagent B were placed at 4 degrees C. (the multiwell plate was in a pouch with desiccant, thus humidity was zero percent). Plates were left at these conditions for thirty additional days.

At the conclusion of the incubation, the dried pellets from each of the conditions were reconstituted using a reconstitution solution containing 100 mM KCl and sufficient $MgCl_2$ for a final concentration of 2.5 mM. Reconstituted reaction mixtures were tested for amplification and detection of an influenza A target using a real-time PCR thermal cycler (ABI PRISM 7000, Applied Biosystems, Carlsbad, CA). Briefly, the influenza A targets were extracted in a negative pool at LOD 10^0 (+/−1 log) along with a comparable liquid control. Results are shown in Table 7.

TABLE 7

| | Average Total RFU<br>(N = 4) |
|---|---|
| Bulk Reagent A<br>4 .deg. C./4 .deg. C. | 1,203,798 |
| Bulk Reagent B<br>4 .deg. C./4 .deg. C. | 255,184 |
| Bulk Reagent A<br>4 .deg. C./15 .deg. C. | 1,012,184 |
| Bulk Reagent B<br>4 .deg. C./15 .deg. C. | 261,882 |
| Bulk Reagent A<br>4 .deg. C./45 .deg. C. | 1,163,704 |
| Bulk Reagent B<br>4 .deg. C./45.deg. C. | 382,725 |

These results show that single amplification reaction dried pellets containing less than 2.5 mM inorganic salts have higher RFU values following storage in a number of different temperature and humidity conditions compared to single amplification reaction dried pellets containing 2.5 mM or more of inorganic salt.

Example 6. Lyophilization of Cleavase® Enzyme Containing Bulk Reagents

A bulk reagent containing the flap endonuclease Cleavase® was manufactured to contain a final glycerol concentration of 0.35%. This bulk reagent was aliquoted and lyophilized as generally described above. Data showed that this level of glycerol content impairs the lyophilization of the SUD pellet by causing what is referred to as "melt back" (data not presented). Melt back generally refers to the collapse of a lyophilized product. Melt back typically results from the presence of a substance during the primary drying phase wherein the substance is detrimental to formation of a robust lyophilized composition. Glycerol is one such substance. Therefore, a solution containing glycerol-free Cleavase® and substantially no inorganic salts was prepared by dialysing the Cleavase® enzyme (which was stored in a 50% glycerol buffer) into a glycerol-free buffer using 20 kDa MWCO Slyde-A-Lyzer cassette system (ThermoFisher P/N #66005). The dialysis buffer composition is listed in Table 8.

TABLE 8

| Cleavase ® dialysis buffer 1 composition | |
|---|---|
| Reagent | Concentration |
| Tris | 20 mM |
| Trehalose | 200 mM |
| KCl | 50 mM |
| EDTA | 0.1 mM |
| pH | 8.0 |

The dialysis of the Cleavase® enzyme in this buffer removed the glycerol and replaced it with the buffer shown in Table 8. The dialyzed Cleavase® enzyme was then used to prepare a glycerol-free bulk reagent with substantially no inorganic salts (Table 9). The bulk reagent was then aliquoted as a number of SUDs into the wells of a multi-well plate and lyophilized. All SUD pellets lyophilized without exhibiting any signs of melt back.

TABLE 9

| 1.25x Pre-lyophilization formulation (version 2 formulation) | | | | |
|---|---|---|---|---|
| Reagent | Vendor & P/N | Stock Conc. | Volume per reaction | Final concentration |
| GoTaq, Glycerol-free (1:10) | Promega X650X | 5 U/µl working stock | 0.67 µl | 0.14 U/µl |
| Cleavase ® 2.0, dialyzed | R&D | 2.0 µg/µl | 0.363 µl | 0.03 µg/µl |
| 10X dNTPs | R&D | 2.5 mM ea | 3.0 µl | 0.313 mM ea |
| 10X *S. aureus* Oligo mix | R&D | 10X | 3.0 µl | 1X |
| MOPS Buffer, pH 7.5 | J62839 | 500 mM | 0.6 µl | 12.5 mM |
| Trehalose | R&D | 1.2M | 6.0 µl | 0.3M |
| Water, MBG | H20MB0106 | — | 10.36 µl | — |

The Oligo mix comprised primers for the PCR reaction, and first probes/second probes/FRET cassettes for the cleavage based assay reaction. The FRET cassettes were each labelled with one of the fluorophore FAM, HEX, or ROX.

Dried compositions containing oligonucleotides for PCR amplification and cleavage-based assay detection of *Staphylococcus aureus* ("*S. aureus*") were rehydrated with a reconstitution solution (stock reconstitution solution comprised 9.375 mM $MgCl_2$, 0.02% (w/v) methyl parapen, 0.01% (w/v) propyl paraben, 0.33% (v/v), and brought to 1 liter total volume using water) to generate a plurality of reaction mastermixes. *S. aureus* target DNA (Positive) or nuclease free water (Negative) was added to separate reconstituted mastermixes and topped with silicone oil. The amplification and detection assays were performed using a Panther Fusion thermocycler. A non-lyophilized bulk reagent was tested in parallel with the lyophilized formulations as a control.

The results in Table 10 below show that in this test the amplification and detection system was able to successfully amplify and detect *S. aureus* positive samples as positive in all three channels and negative samples as negative in all three channels and with comparable values compared to the wet mix control.

TABLE 10

| Testing of bulk reagent version 2 - lyophilized vs non-lyophilized control | | | | | | | |
|---|---|---|---|---|---|---|---|
| Format | Sample | FAM Ct | FAM RFU | HEX Ct | HEX RFU | ROX Ct | ROX RFU |
| Non-lyophilized control | Negative | not detected | 918 | not detected | 329 | not detected | 137 |
| | Positive | 30.0 | 25,977 | 32.0 | 9,006 | 32.4 | 2,142 |
| | Positive | 29.5 | 29,762 | 31.6 | 10,692 | 32.0 | 2,536 |
| Lyophilized | Negative | not detected | 495 | not detected | 308 | not detected | 110 |
| | Positive | 31.1 | 16,924 | 33.2 | 4,672 | 34.4 | 1,329 |
| | Positive | 30.4 | 19,403 | 32.5 | 5,915 | 33.6 | 1,559 |

Example 7. Cleavase® Pre-Lyophilization Formulation Version 3

A revised version of the *S. aureus* pre-lyophilization formulation was made that included ultrapure non-acetylated BSA and a buffer change from MOPS buffer to Tris buffer (Table 11).

TABLE 11

1.25x pre-lyophilized formulation (version 3 formulation) using 2X MMA GoTaq source

| Reagent | Vendor & P/N | Stock Conc. | Volume per pre-lyo reaction | Final Conc. in pre-lyo mix |
|---|---|---|---|---|
| GoTaq, Glycerol-free, 2X Mastermix A | Promega X991X | 0.74 U/μl | 4.75 μl | 0.146 U/μl |
| Cleavase ® 2.0, dialyzed | R&D | 2.2 μg/μl | 0.33 μl | 0.03 μg/μl |
| BSA, Ultrapure non-acetylated * | Ambion | 50 μg/μl | 0.20 μl | ~0.5 μg/μl ZZZZZ ZZZZZ |
| 10X dNTPs * | R&D | 2.5 mM ea | 2.24 μl | ~0.31 mM ea |
| 10X *S. aureus* Oligo mix | R&D | 10X | 3.0 μl | 1X |
| Tris Buffer, pH 8.5 * | R&D | 1.0M | 1.0 μl | ~50 mM |
| Trehalose * | R&D | 1.2M | 4.1 μl | 0.3M |
| Water, MBG | H20MB0106 | — | 8.24 μl | — |

* The formulation in Table 11 was supplemented with Trehalose, Tris buffer, dNTPs and non-acetyltated BSA. These reagents were added to supplement material already included in the Promega 2X Mastermix reagent.

Promega X991X was formulated as a 2× Mastermix which when diluted 1:1 would yield a reaction mix with 0.24M Trehalose, 0.2 mM dNTPs (0.4 mM dUTP), and 9.25 U GoTaq, as well as non-acetylated BSA and Tris in a 25 ul reaction mixture. A total of 25 cartridges from this formulation were prepared and successfully lyophilized.

Amplification and detection reactions were prepared and performed as is generally described above in Example 6. Lyophilized pellets were reconstituted using a reconstitution solution similar to that described in Example 6, except that the concentration of MgCl$_2$ was increased to provide 12.5 mM MgCl$_2$ in the reconstituted reaction mixture. As a control, a number of non-lyophilized reaction mixtures were prepared and tested. The *S. aureus* target nucleic acid used in these reactions was *S. aureus* gDNA at 100 copies/mL and at 1,000 copies/mL (approximately 3 times the assay LoD for this target). In the presence of 12.5 mM MgCl$_2$, Tris buffered reactions showed delayed Cts, reduced RFUs and reduced T-slope values for the *S. aureus* positive samples. Further, the negative samples using the Tris buffer formulation showed elevated background generation compared to negative samples using a 10 mM MOPS buffer formaltion—irrespective of the MgCl$_2$ concentration in the reaction mixture. Thus, based upon these results, MOPS buffer offers advantages for use in the bulk formulation and can be used at a concentration of up to about 15 mM in a final cartridge formulation.

The formulation illustrated in Table 11 was further varied and was tested. Formulation variations were prepared as a series of bulk reagents wherein the 11% trehalose was substituted with various trehalose/sugar/polymer combinations. These bulk reagent formulations contained the following reagent combinations and were lyophilized and tested as described above:

a) 3% Trehalose/1% 10 kDa polyvinyl propylene.
b) 3% Trehalose/2% 10 kDa polyvinyl propylene.
c) 3% Trehalose/3% 10 kDa polyvinyl propylene.
d) 3% Trehalose/1% 29 kDa polyvinyl propylene.
e) 3% Trehalose/2% 29 kDa polyvinyl propylene.
f) 3% Trehalose/3% 29 kDa polyvinyl propylene.
g) 3% Trehalose/1% 55 kDa polyvinyl propylene.
h) 3% Trehalose/2% 55 kDa polyvinyl propylene.
i) 3% Trehalose/3% 55 kDa polyvinyl propylene.
j) 3% Trehalose/1% Sucrose.
k) 3% Trehalose/2% Sucrose.
l) 3% Trehalose/3% Sucrose.
m) 11% Trehalose (Control).

Except for the condition i) and Control condition m), all combinations lyophilized well and did not show any initial collapse. Functional testing at t=0 also showed that there was no significant Ct delay in any of combinations a) through m). However, when placed under accelerated stability at 37 degrees C./95% RH, all combinations, except the control condition, exhibited collapse after 4 days. The control cartridge with 11% trehalose did not show collapse at 37 degrees C./95% RH until 14-16 days. Thus, bulk reagent formulations containing 11% are suitable for long term storage of lyophilized pellets before use.

Example 8. Cleavase® Pre-Lyophilization Formulation Version 4

It is desirable to alter a sample input volume. Lower sample volumes are useful to accommodate multiple tests on a patient sample. Sample input volumes between 210 ul and 420 ul were tested. In order to retain sensitivity at the lower sample draw volume, the eluate volume used in the PCR reaction was increased from 5 ul to 10 ul. The extra 5 ul of eluate sample changes the concentrations of the reagents in the reaction mixture. The reagent concentrations for the bulk reagent were adjusted to account for the different eluate volume (see Table 13).

A comparison of the 420 ul/5 ul vs 210 ul/10 ul conditions showed that performance was equivalent for both conditions (Table 12):

TABLE 12

| 420/5 μl vs 210/10 μl | | | | | |
|---|---|---|---|---|---|
| | CFU/mL | n | FAM Pos | HEX Pos | ROX Pos |
| % POS | | | | | |
| Control (420/5) | 0 | 12 | 0% | 0% | 0% |
| | 100 | 18 | 0% | 0% | 78% |
| | 400 | 18 | 0% | 11% | 100% |
| Modified (210/10) | 100 | 18 | 0% | 11% | 78% |
| | 400 | 18 | 0% | 22% | 100% |

TABLE 12-continued

| | 420/5 µl vs 210/10 µl | | | | |
|---|---|---|---|---|---|
| | CFU/mL | n | FAM Pos | HEX Pos | ROX Pos |
| Ct | | | | | |
| Control | 0 | 12 | — | — | — |
| (420/5) | 100 | 18 | — | — | 39.8 |
| | 400 | 18 | — | 40.9 | 37.7 |
| Modified | 100 | 18 | — | 40.0 | 39.3 |
| (210/10) | 400 | 18 | — | 40.4 | 37.3 |
| RFU | | | | | |
| Control | 0 | 12 | — | — | — |
| (420/5) | 100 | 18 | — | — | 1514 |
| | 400 | 18 | — | 9870 | 2030 |
| Modified | 100 | 18 | — | 8893 | 1645 |
| (210/10) | 400 | 18 | — | 3780 | 2169 |

Increasing the eluate volume from 5 ul up to 10 ul resulted in a change in the SUD pellet concentration to "1.5×" in order to provide a total reaction mixture volume of 30 ul (e.g., 20 ul mastermix+10 ul eluate). Table 13 reflects the volume change and also replaces Tris buffer with 10 mM MOPS buffer, pH 7.5.

TABLE 13

1.5x *S. aureus* pre-lyo formulation version 4 with MOPS buffer

| Reagent | Vendor & P/N | Stock Conc. | Volume per pre-lyo reaction | Final Conc. in pre-lyo mix |
|---|---|---|---|---|
| GoTaq, Glycerol-free, 2X Mastermix A | Promega X991X | 0.74 U/µl | 5.47 µl | 0.1687 U/µl |
| Cleavase ® 2.0, dialyzed | R&D | 1.82 µg/µl | 0.46 µl | 0.035 µg/µl |
| BSA, Ultrapure non-acetylated * | Ambion | 50 µg/µl | 0.24 µl | ~0.509 µg/µl |
| 10X dNTPs * | R&D | 2.5 mM ea | 2.73 µl | ~0.375 mM ea |
| 10X *S. aureus* Oligo mix | R&D | 10X | 3.6 µl | 1X |
| EDTA/EGTA, 0.1M | 101068 | 0.1M ea | 0.036 µl | 0.15 mM ea |
| MOPS buffer, pH 7.5 | R&D | 500 mM | 0.72 µl | 15 mM |
| Trehalose * | R&D | 1.2M | 5.01 µl | 0.36M |
| Water, MBG | H20MB0106 | — | 5.77 µl | — |

* These reagents are added to supplement material already included in the 2X Mastermix A reagent.

This version 4 formulation has more concentrated reagents to accommodate a doubling in sample eluate volume for the PCR reaction (5 µl→10 µl). With the change in concentrations of the formulation, a new hold time study was performed to ensure formulation robustness. On Day 0, a liquid *S. aureus* reaction mix was prepared according to Table 13 above, and split into 3 aliquots. The first aliquot was lyophilized immediately, the second aliquot of the mix was lyophilized after 2 days storage at 2-8 degrees C., and the last aliquot was lyophilized after 4 days storage at 2-8 degrees C. The resulting cartridges were sealed and tested at baseline (data not shown), and also subjected to 4 weeks accelerated stability at 30 degrees C./95% Relative Humidity (RH). Testing was carried out using MRSA cell strain at 0.5 logs above the LoD (1,000 CFU/mL), in 10 replicates per condition. The results showed that this formulation is able to detect MRSA at 0.5 log above the LoD and demonstrates robustness with regards to a 0-4 days hold time prior to lyophilization, and up to 30 days of accelerated stability at 30 degrees C./95% RH after lyophilization.

Example 9

Alpha-cyclodextrin can be added to a composition to be lyophilized to counter the inhibitory effect of a substance like SDS, which can be used to wash captured nucleic acids. Some of the SDS will remain in the nucleic acid solution, and subsequently in the nucleic acid amplification and detection reaction. We first prepared four versions of a formulation using *S. aureus* cells (GP1822) at 1,000 CFU/mL in Simulated Nasal Fluid (SNF) similar to that in Table 13, with the following differences (1) 0 ug/ul cyclodextrin; (2) 0.1 ug/ul cyclodextrin; (3) 0.25 ug/ul cyclodextrin; or (4) 0.5 ug/ul cyclodextrin. The specimens were processed on the Panther Fusion Instrument (P182). The 30% wash buffer was spiked into the elution buffer (i.e. normal WB carry over +30%). The pellets were then used in test reactions for the amplification and detection of a MRSA target nucleic acid. No SDS was added to these amplification reaction. This experiment determines if the addition of cyclodextrin to the mixtures had an impact on a nucleic acid reaction performed with the pellet. As can be seen in conditions 1-4 of Table 14 the ct values were substantially identical for each of the test conditions, indicating that there is no negative impact on the performance of a pellet containing at least as much as 0.5 ug/ul of cyclodextrin.

Following the first experiments four versions of formulation similar to that in Table 13 were again prepared and contained one of (1) 0 ug/ul cyclodextrin; (2) 0.1 ug/ul cyclodextrin; (3) 0.25 ug/ul cyclodextrin; or (4) 0.5 ug/ul cyclodextrin. The resulting pellets were then used in test reactions for the amplification and detection of a MRSA target nucleic acid. To this set of amplification reactions, SDS was added to a final concentration of 30% v/v in to the reaction mix. Amplification and detection reactions were performed. As can be seen in conditions 5-8 of Table 14, the SDS has an inhibitory effect on the nucleic acid reaction (condition 5). 0.1 ug/ul cyclodextrin almost completely neutralized the inhibition of the SDS (condition 6), and 0.25 ug/ul and 0.5 ug/ul fully neutralized the inhibition of the SDS (conditions 7 & 8).

TABLE 14

| cyclodextrin-alpha conc. | | n | FAM | | | HEX | | | ROX | | | RED677 | | |
|---|---|---|---|---|---|---|---|---|---|---|---|---|---|---|
| | | | n pos | Avg. CT | Ct Std Dev. | n pos | Avg. Ct | Ct Std Dev. | n pos | Avg. Ct | Ct Std Dev. | n pos | Avg. Ct | Ct Std Dev. |
| 0% Wash Buffer | 0 ug/ul | 24 | 24 | 34.22 | 1.12 | 24 | 34.82 | 0.39 | 24 | 33.75 | 0.40 | 24 | 31.78 | 1.37 |
| | 0.10 ug/ul | 24 | 24 | 34.18 | 0.61 | 24 | 35.03 | 0.42 | 24 | 33.86 | 0.48 | 24 | 31.6 | 0.92 |
| | 0.25 ug/ul | 24 | 24 | 33.95 | 0.52 | 24 | 35.08 | 0.31 | 34 | 33.78 | 0.44 | 24 | 31.32 | 1.01 |
| | 0.50 ug/ul | 24 | 24 | 33.79 | 0.32 | 24 | 34.88 | 0.28 | 24 | 33.73 | 0.39 | 24 | 31.18 | 0.36 |
| 30% Wash Buffer | 0 ug/ul | 24 | 0 | — | — | 24 | 39.79 | 1.84 | 24 | 37.97 | 2.44 | 20 | 37.86 | 4.30 |
| | 0.10 ug/ul | 24 | 22 | 36.96 | 1.56 | 24 | 37.73 | 0.92 | 24 | 36.33 | 0.83 | 24 | 33.53 | 1.35 |
| | 0.25 ug/ul | 24 | 24 | 35.00 | 2.24 | 24 | 35.43 | 0.31 | 24 | 34.56 | 0.30 | 24 | 32.06 | 1.22 |
| | 0.50 ug/ul | 24 | 24 | 34.63 | 0.69 | 24 | 35.78 | 0.92 | 24 | 34.71 | 0.82 | 24 | 32.88 | 0.99 |

A further data set was tested also using *S. aureus* cells (GP1822) at 1,000 CFU/mL in Simulated Nasal Fluid (SNF). The specimens were processed on the Panther Fusion Instrument (P368). The 30% wash buffer was spiked into the elution buffer (i.e. normal WB carry over +30%).

TABLE 15

| cyclodextrin-alpha conc. | | n | FAM | | | HEX | | | ROX | | | RED677 | | |
|---|---|---|---|---|---|---|---|---|---|---|---|---|---|---|
| | | | n pos | Avg. CT | Ct Std Dev. | n pos | Avg. Ct | Ct Std Dev. | n pos | Avg. Ct | Ct Std Dev. | n pos | Avg. Ct | Ct Std Dev. |
| 0% Wash Buffer | 0.01 ug/ul | 12 | 12 | 37.77 | 0.96 | 12 | 38.93 | 0.62 | 12 | 38.38 | 0.63 | 12 | 40.48 | 1.37 |
| | 0.05 ug/ul | 12 | 12 | 37.38 | 0.67 | 12 | 39.08 | 0.52 | 12 | 38.19 | 0.79 | 12 | 40.15 | 0.47 |
| | 0.10 ug/ul | 12 | 12 | 37.55 | 0.70 | 12 | 38.65 | 0.42 | 12 | 37.93 | 0.48 | 12 | 39.92 | 0.73 |
| | 0.25 ug/ul | 12 | 12 | 37.60 | 0.60 | 12 | 38.97 | 0.99 | 12 | 38.24 | 0.50 | 12 | 40.25 | 0.77 |
| | 1.00 ug/ul | 12 | 12 | 37.17 | 0.60 | 12 | 38.84 | 0.69 | 12 | 38.21 | 0.94 | 12 | 39.62 | 0.85 |
| | 3.00 ug/ul | 12 | 11 | 38.14 | 1.90 | 12 | 39.03 | 0.96 | 12 | 37.83 | 0.68 | 12 | 40.37 | 1.07 |
| | 5.00 ug/ul | 12 | 12 | 37.19 | 0.60 | 12 | 38.71 | 0.73 | 12 | 38.00 | 1.07 | 12 | 39.67 | 0.82 |
| 30% Wash Buffer | 0.01 ug/ul | 12 | 3 | 43.33 | 1.34 | 11 | 43.09 | 0.91 | 11 | 41.13 | 1.71 | 5 | 46.70 | 1.59 |
| | 0.05 ug/ul | 12 | 7 | 42.77 | 3.09 | 12 | 42.70 | 0.90 | 12 | 40.85 | 1.31 | 9 | 46.57 | 4.30 |
| | 0.10 ug/ul | 12 | 11 | 40.84 | 1.21 | 12 | 42.38 | 0.67 | 12 | 40.39 | 0.43 | 12 | 44.95 | 1.82 |
| | 0.25 ug/ul | 12 | 12 | 39.81 | 0.69 | 12 | 42.33 | 0.92 | 12 | 40.14 | 0.69 | 12 | 42.98 | 1.31 |
| | 1.00 ug/ul | 12 | 12 | 38.20 | 0.64 | 12 | 40.18 | 0.54 | 12 | 39.23 | 0.34 | 12 | 41.17 | 0.93 |
| | 3.00 ug/ul | 12 | 12 | 37.84 | 0.61 | 12 | 39.69 | 0.57 | 12 | 38.59 | 0.52 | 12 | 41.78 | 0.96 |
| | 5.00 ug/ul | 12 | 12 | 37.43 | 0.50 | 12 | 39.43 | 0.40 | 12 | 38.54 | 0.56 | 12 | 41.31 | 0.95 |

The table shows higher concentrations of cyclodextrin up to 5.0 ug/ml are effective in neutralizing SDS.

Thus, formulations such as those in Table 13 can be supplemented with cyclodextrin, e.g., at 0.1 to 5 ug/ul, or 0.1 to 0.5 cyclodextrin.

From the foregoing, it will be appreciated that, although specific embodiments have been described herein for purposes of illustration, various modifications may be made without deviating from the spirit and scope of this explicit disclosure. Accordingly, the invention is not limited by the explicit disclosure. Unless otherwise apparent from the context any embodiment, feature, aspect or step can be used in combination with any other. Unless otherwise apparent from the context, any composition said to comprise enumerated components may also consist or consist essentially of those components All publications, patents, and patent applications cited herein are hereby incorporated by reference in their entireties for all purposes.

The invention claimed is:

1. A kit for use in performing a nucleic acid based assay, the kit comprising a first vessel containing adried composition, and a second vessel containing a reconstitution solution; wherein the dried composition comprises a bulking agent, a flap-endonuclease, dNTPs, a chelating agent, 3-(N-morpholino)propanesulfonic acid (MOPS) or tris(hydroxymethyl)aminomethane (Tris), and contains substantially no magnesium ions; and wherein the reconstitution solution comprises $MgCl_2$ at a concentration from about 3.8 mM to about 4.4 mM.

2. The kit of claim 1, wherein the first vessel is a multiwell plate, wherein one or more wells of the multiwell plate contain a unit dose of the dried composition.

3. The kit of claim 1, wherein the percent mass of inorganic salt is 0.35% or less, 0.311% or less, 0.249% or less, 0.186% or less, 0.124% or less, 0.062% or less, or 0.031% or less.

4. The kit of claim 1, wherein the first and second vessels are configured for use in a device adapted for automated transfer of the reconstitution solution from the second vessel into the first vessel.

5. The kit of claim 1, wherein the bulking agent is selected from the group consisting of: raffinose, sucrose, mannitol, trehalose, and combinations thereof.

6. The kit of claim 5, wherein the bulking agent is raffinose, trehalose or a combination of raffinose and trehalose.

7. The kit of claim 1, wherein the dried composition further comprises one or more oligonucleotides selected from the group consisting of: an amplification oligomer, a detection probe, a signal probe, a FRET probe, and invader probe, and combinations thereof.

8. The kit of claim 1, wherein the dried composition further comprises at least two probe oligonucleotides capable of annealing to a target nucleic acid to form a three-dimensional structure that can be recognized by the flap endonuclease.

9. The kit of claim 1, wherein the dried composition further comprises a reverse transcriptase or an RNase inhibitor.

10. The kit of claim 1, wherein the dNTPs include dTTP and dUTP.

11. The kit of claim 1, wherein the chelating agent is selected from the group consisting of: ethylenediaminetetraacetic acid (EDTA), ethylene glycol tetraacetic acid (EGTA), ethylenediamine-N,N'-disuccinic acid (EDDS), methylglycindiacetic acid (MGDA), diethylene triamine pentaacetic acid (DTPA), and combinations thereof.

12. The kit of claim 1, wherein the dried composition further contains a reverse transcriptase and an RNase inhibitor.

13. The kit of claim 12, wherein the percent mass of inorganic salt is 0.35% or less, 0.311% or less, 0.249% or less, 0.186% or less, 0.124% or less, 0.062% or less, or 0.031% or less.

14. The kit of claim 12, wherein the bulking agent is selected from the group consisting of: raffinose, sucrose, mannitol, trehalose, and combinations thereof.

15. The kit of claim 14, wherein the bulking agent is raffinose, trehalose, or a combination of raffinose and trehalose.

16. The kit of claim 12, wherein the dried composition further comprises an oligonucleotide selected from the group consisting of: an amplification oligomer, a detection probe, a signal probe, a FRET probe, and invader probe, and combinations thereof.

17. The kit of claim 12, wherein the dNTPs include dTTP and dUTP.

18. The kit of claim 12, wherein the chelating agent is selected from the group consisting of EDTA, EGTA, EDDS, MGDA, DTPA, and combinations thereof.

19. The kit of claim 12, wherein the first vessel is a multiwell plate comprising, wherein one or more wells of the multiwell plate contain a unit dose of the dried composition.

20. The kit of claim 12, wherein the first and second vessels are configured for use in a device adapted for automated transfer of the reconstitution solution from the second vessel into the first vessel.

21. A kit for use in performing a non-nucleic acid based assay, the kit comprising a first vessel containing a dried composition and a second vessel containing a reconstitution solution; wherein the dried composition comprises a bulking agent, a flap-endonuclease, a DNA polymerase, dNTPs, a chelating agent, 3-(N-morpholino)propanesulfonic acid (MOPS) or tris(hydroxymethyl)aminomethane (Tris), and contains substantially no magnesium ions; and wherein the reconstitution solution comprises $MgCl_2$ at a concentration from about 3.8 mM to about 4.4 mM.

* * * * *

UNITED STATES PATENT AND TRADEMARK OFFICE
CERTIFICATE OF CORRECTION

PATENT NO. : 11,952,630 B2
APPLICATION NO. : 17/746400
DATED : April 9, 2024
INVENTOR(S) : Patrick Peterson et al.

Page 1 of 2

It is certified that error appears in the above-identified patent and that said Letters Patent is hereby corrected as shown below:

In the Specification

In Column 1, Line 8, delete "2022," and insert -- 2022, now abandoned, --, therefor.
In Column 2, Line 1, delete "No." and insert -- Nos. --, therefor.
In Column 2, Line 36, delete "lyopholized" and insert -- lyophilized --, therefor.
In Column 6, Line 10, delete "µg/µ1," and insert -- µg/µl, --, therefor.
In Column 6, Line 16, delete "µg/µ1," and insert -- µg/µl, --, therefor.
In Column 8, Lines 30-31, delete "FRET-probe." and insert -- FRET probe. --, therefor.
In Column 8, Line 34, delete "molecule" and insert -- molecule. --, therefor.
In Column 10, Line 63, delete "lyphophilized" and insert -- lyophilized --, therefor.
In Column 13, Line 62, delete "Cl—" and insert -- Cl⁻ --, therefor.
In Column 14, Line 42, delete "e.g.," and insert -- (e.g., --, therefor.
In Column 16, Line 15, delete "437:51);" and insert -- 437:51; --, therefor.
In Column 16, Line 23, delete "one more" and insert -- one or more --, therefor.
In Column 16, Line 26, delete "one more" and insert -- one or more --, therefor.
In Column 16, Line 29, delete "one more" and insert -- one or more --, therefor.
In Column 16, Line 57, delete "(methylglycindiacetic acid)," and insert -- (methylglycinediacetic acid), --, therefor.
In Column 17, Line 14, delete "Luviquat™," and insert -- luviquat™, --, therefor.
In Column 17, Line 57, delete "dGTP dCTP" and insert -- dGTP, dCTP --, therefor.
In Column 17, Line 66, delete "dGTP dCTP" and insert -- dGTP, dCTP --, therefor.
In Column 18, Line 10, delete "dGTP dCTP" and insert -- dGTP, dCTP --, therefor.
In Column 18, Line 20, delete "dGTP dCTP" and insert -- dGTP, dCTP --, therefor.
In Column 18, Line 34, delete "dGTP dCTP" and insert -- dGTP, dCTP --, therefor.
In Column 18, Line 49, delete "dGTP dCTP" and insert -- dGTP, dCTP --, therefor.
In Column 18, Line 62, delete "dGTP dCTP" and insert -- dGTP, dCTP --, therefor.
In Column 19, Line 9, delete "dGTP dCTP" and insert -- dGTP, dCTP --, therefor.
In Column 19, Line 23, delete "dGTP dCTP" and insert -- dGTP, dCTP --, therefor.
In Column 19, Line 36, delete "dGTP dCTP" and insert -- dGTP, dCTP --, therefor.
In Column 20, Line 9, delete "pellet" and insert -- pellet. --, therefor.

Signed and Sealed this
Eighteenth Day of June, 2024

Katherine Kelly Vidal
*Director of the United States Patent and Trademark Office*

CERTIFICATE OF CORRECTION (continued)
U.S. Pat. No. 11,952,630 B2

In Column 25, Line 59, delete "PA" and insert -- PA. --, therefor.
In Column 26, Line 51, delete "99% the value before immediately" and insert -- 99% of the value immediately --, therefor.
In Column 28, Line 8, delete "PA" and insert -- PA. --, therefor.
In Column 28, Line 10, delete "composition" and insert -- composition. --, therefor.
In Columns 31-32, in "Table 3", Line 6, delete "withoutMgCl$_2$)" and insert -- without MgCl$_2$) --, therefor.
In Column 35, Line 48, delete "above" and insert -- above. --, therefor.
In Column 38, Line 40, delete "parapen," and insert -- paraben, --, therefor.
In Columns 39-40, Table 11, Line 16, below "~0.5 µg/µl", delete "ZZZZZ ZZZZZ".
In Columns 39-40, Table 11, Line 22, delete "non-acetyltated" and insert -- non-acetylated --, therefor.
In Column 39, Line 47, delete "formaltion" and insert -- formulation --, therefor.
In Column 42, Line 57, delete "in to" and insert -- into --, therefor.
In Columns 43-44, in "Table 14", Line 2, delete "cyclodcxtrin" and insert -- cyclodextrin --, therefor.

In the Claims

In Column 43, Line 64, in Claim 1, delete "adried" and insert -- a dried --, therefor.
In Column 44, Line 56, in Claim 6, delete "trehalose" and insert -- trehalose, --, therefor.
In Column 45, Line 10, in Claim 11, delete "methylglycindiacetic" and insert -- methylglycinediacetic --, therefor.